United States Patent
Kim

(10) Patent No.: US 9,820,705 B2
(45) Date of Patent: Nov. 21, 2017

(54) X-RAY PHOTOGRAPHING APPARATUS AND COLLIMATOR

(71) Applicant: SAMSUNG ELECTRONICS CO., LTD., Suwon-si (KR)

(72) Inventor: Dong-hwan Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 57 days.

(21) Appl. No.: 14/941,922

(22) Filed: Nov. 16, 2015

(65) Prior Publication Data

US 2016/0135767 A1  May 19, 2016

(30) Foreign Application Priority Data

Nov. 14, 2014  (KR) .................. 10-2014-0158909

(51) Int. Cl.
| | |
|---|---|
| *A61B 6/08* | (2006.01) |
| *A61B 6/00* | (2006.01) |
| *A61B 6/06* | (2006.01) |
| *G03B 21/20* | (2006.01) |
| *G03B 21/28* | (2006.01) |
| *G03B 29/00* | (2006.01) |

(Continued)

(52) U.S. Cl.
CPC ............ *A61B 6/4417* (2013.01); *A61B 6/06* (2013.01); *A61B 6/08* (2013.01); *G03B 21/208* (2013.01); *G03B 21/28* (2013.01); *G03B 29/00* (2013.01); *G21K 1/04* (2013.01); *H01J 35/00* (2013.01); *A61B 6/461* (2013.01); *A61B 6/467* (2013.01); *A61B 6/542* (2013.01)

(58) Field of Classification Search
CPC ......... A61B 6/547; A61B 6/0492; A61B 6/08; A61B 6/587; A61B 6/4405; A61B 6/4441; A61B 6/583
USPC .................................................. 378/205, 206
See application file for complete search history.

(56) References Cited

U.S. PATENT DOCUMENTS

| | | | |
|---|---|---|---|
| 4,167,675 A | 9/1979 | Stoberg et al. | |
| 5,311,568 A * | 5/1994 | McKee, Jr. ............. | H05G 1/64 |
| | | | 250/214 VT |

(Continued)

FOREIGN PATENT DOCUMENTS

| | | |
|---|---|---|
| JP | 2006-334096 A | 12/2006 |
| JP | 2007-199542 A | 8/2007 |
| WO | 2011/107111 A1 | 9/2011 |

OTHER PUBLICATIONS

Communication dated Mar. 8, 2016, issued by the International Searching Authority in counterpart International Application No. PCT/KR2015/012215 (PCT/ISA/220, 210, 237).

*Primary Examiner* — Don Wong
(74) *Attorney, Agent, or Firm* — Sughrue Mion, PLLC

(57) ABSTRACT

Provided is an X-ray photographing apparatus including an X-ray source for generating and irradiating an X-ray; a collimator for controlling an X-ray photographing area to which an X-ray is irradiated by the X-ray source; a projector for generating and projecting a visible ray image by using image signals; a reflection mirror for reflecting the visible ray image projected by the projector to an X-ray photographing area; and a main controller for controlling the projector to match a light irradiation field corresponding to the visible ray image projected to the X-ray photographing area to the X-ray irradiation field.

13 Claims, 31 Drawing Sheets

(51) Int. Cl.
*G21K 1/04* (2006.01)
*H01J 35/00* (2006.01)

(56) References Cited

U.S. PATENT DOCUMENTS

| | | | |
|---|---|---|---|
| 2009/0190722 A1* | 7/2009 | Windt | A61B 6/08 378/206 |
| 2011/0305320 A1 | 12/2011 | Suuronen et al. | |
| 2012/0039447 A1 | 2/2012 | Lalena et al. | |

* cited by examiner

X-RAY PHOTOGRAPHING APPARATUS AND COLLIMATOR

CROSS-REFERENCE TO RELATED APPLICATIONS

This application claims priority from Korean Patent Application No. 10-2014-0158909, filed on Nov. 14, 2014, in the Korean Intellectual Property Office, the disclosure of which is incorporated herein by reference in its entirety.

BACKGROUND

1. Field

Apparatuses and methods consistent with the exemplary embodiments relate to an X-ray photographing apparatus and a collimator, and more particularly, to an X-ray photographing apparatus and a collimator that use an image of visible rays irradiated from a projector for overlapping an X-ray irradiation field and a light irradiation field.

2. Description of the Related Art

Generally, demand for devices for photographing a target object by using an X-ray is rapidly increasing as medical care is improved based on rapid industrial growth, and thus demand for medical X-ray photographing apparatuses is increasing day by day.

A medical X-ray photographing apparatus is an apparatus for photographing the interior of a human body by irradiating an X-ray with excellent penetrability to a region of the human body. X-rays are a type of radioactive waves, and tissues may be damaged and various illnesses caused from extended exposure to radioactive waves.

To prevent such illnesses, an X-ray photographing apparatus includes an X-ray irradiation range controlling device for minimizing side effects based on X-ray exposure of a patient.

Most medical X-ray photographing apparatuses use collimators, and such a collimator includes an aperture in a vertical direction to adjust a vertical or horizontal range of an X-ray, thereby suitably adjusting an area of irradiation of an X-ray.

For example, in some photographing methods, it is necessary to manually or automatically adjust an area of irradiation of a collimator to restrict an area of irradiation of an X-ray to a particular area, and it is necessary to confirm location of the area based on light from a collimator. The above-stated operations are necessary for a precise photographing operation. However, it may be inconvenient for a user due to a long period of time taken for a photographing operation and multiple operations.

SUMMARY

According to an aspect of an exemplary embodiment, an X-ray photographing apparatus includes an X-ray source for generating and irradiating an X-ray; a collimator for controlling an X-ray photographing area to which an X-ray is irradiated by the X-ray source; a projector for generating and projecting a visible ray image by using image signals; a reflection mirror for reflecting the visible ray image projected by the projector to an X-ray photographing area; and a main controller for controlling the projector to match a light irradiation field corresponding to the visible ray image projected to the X-ray photographing area to the X-ray irradiation field.

The projector includes an image generating unit for generating the visible ray image by using the image signals; a lens unit, which consists of a plurality of lenses and focuses a visible ray image generated by the image generating unit; and a projector controller for controlling at least one of the image generating unit and the lens unit.

The image generating unit includes a display device for converting the image signals to a projection image; and a light source for providing a light for generating the projection image converted by the display device as a visible ray image, and the image signals are converted to the projection image at an active area, which is a portion of the display device.

The projector controller controls location of the active area on the display device, thereby controlling location of the visible ray image projected by the projector.

The projector controller controls distances between the plurality of lenses, thereby controlling size of the visible ray image projected by the projector.

The projector controller controls the distances between the plurality of lenses, thereby controlling focus of the visible ray image projected by the projector.

The display device is a deformable mirror device (DMD).

The display device is a liquid crystal on silicon (LCos).

The display device 605 is an organic light emitting diode (OLED).

The visible ray image includes information regarding a photographing operation of the X-ray photographing apparatus or information regarding a target object to be photographed by the X-ray photographing apparatus.

A collimator for controlling an X-ray irradiation field, to which an X-ray is irradiated by an X-ray source, the collimator includes an image generating unit for generating a visible ray image by using image signals; a lens unit, which consists of a plurality of lenses and focuses the visible ray image; a reflection mirror for reflecting the visible ray image irradiated by the lens unit to an X-ray photographing area; and a projector controller, which controls at least one of the image generating unit and the lens unit to match a light irradiation field corresponding to the visible ray image projected to the X-ray photographing area to the X-ray irradiation field.

The image generating unit includes a display device for converting the image signals to a projection image; and a light source for providing a light for generating the projection image converted by the display device as a visible ray image, and the image signals are converted to the projection image at an active area, which is a portion of the display device.

The projector controller controls location of the active area on the display device, thereby controlling location of the visible ray image projected by the lens unit.

The projector controller controls distances between the plurality of lenses, thereby controlling size of the visible ray image projected by the lens unit.

The display device is a deformable mirror device (DMD).

The display device is a liquid crystal on silicon (LCos).

The display device 605 is an organic light emitting diode (OLED).

The X-ray photographing apparatus further includes an optical apparatus, which is located close to the reflection mirror and focuses a photographing light corresponding to the X-ray photographing area; and an image sensor, which receives the photographing light focused at the optical apparatus.

The main controller adjusts a path in which the photographing light travels and a path in which a projection light irradiated by the lens unit travels by adjusting orientation of the optical apparatus.

The optical apparatus is a revolving mirror.

The optical apparatus is a beam splitter.

The projector further includes an image sensor for receiving a light reflected by the display device, the lens unit focuses a photographing light corresponding to an X-ray photographing area, and the display device reflects the photographing light focused at the lens unit to the image sensor.

The collimator further includes an optical apparatus, which is located close to the reflection mirror and focuses a photographing light corresponding to the X-ray photographing area; and an image sensor, which receives the photographing light focused at the optical apparatus.

The projector controller adjusts a path in which the photographing light travels and a path in which a projection light irradiated by the lens unit travels by adjusting orientation of the optical apparatus.

The optical apparatus is a revolving mirror.

The optical apparatus is a beam splitter.

The projector further includes an image sensor for receiving a light reflected by the display device, the lens unit focuses a photographing light corresponding to an X-ray photographing area, and the display device reflects the photographing light focused at the lens unit to the image sensor.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
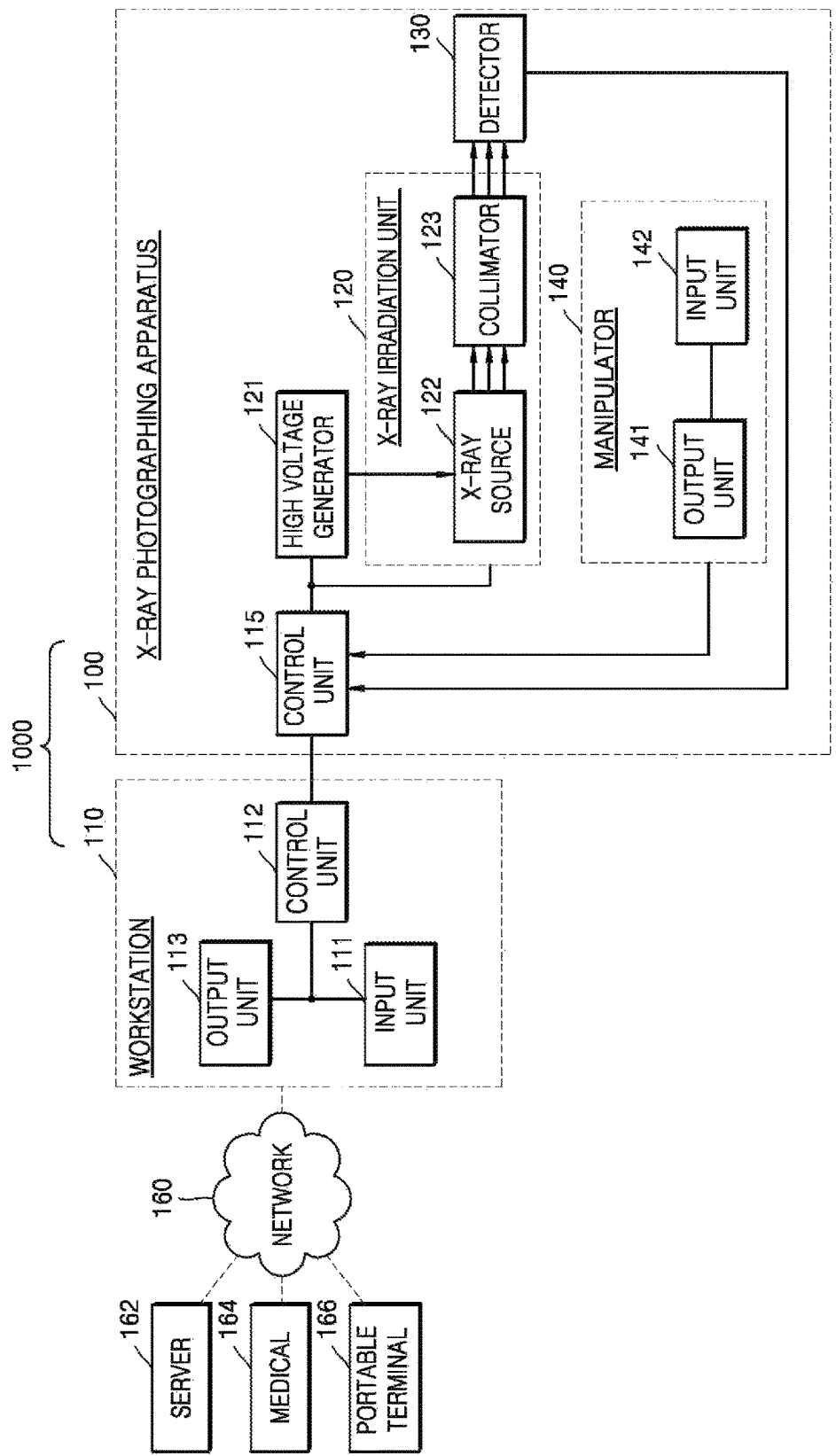
FIG. 1 is a block diagram of an X-ray photographing apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments. As used herein, the term "and/or" includes any and all combinations of one or more of the associated listed items. Expressions such as "at least one of," when preceding a list of elements, modify the entire list of elements and do not modify the individual elements of the list.

The attached drawings for illustrating exemplary embodiments are referred to in order to gain a sufficient understanding of the exemplary embodiments, the merits thereof, and the objectives accomplished by the implementation of the exemplary embodiments. The exemplary embodiments may, however, be embodied in many different forms and should not be construed as being limited to the embodiments set forth herein; rather, these embodiments are provided such that this disclosure will be thorough and complete, and will fully convey the concept of the invention to one of ordinary skill in the art.

Hereinafter, the terms used in the specification will be briefly described, and then the exemplary embodiments will be described in detail.

The terms used in this specification are those general terms currently widely used in the art in consideration of functions in regard to the exemplary embodiments, but the terms may vary according to the intention of those of ordinary skill in the art, precedents, or new technology in the art. Also, specified terms may be selected by the applicant, and in this case, the detailed meaning thereof will be described in the detailed description of the exemplary embodiments. Thus, the terms used in the specification should be understood not as simple names but based on the meaning of the terms and the overall description of the exemplary embodiments.

In the present specification, an "image" may denote multi-dimensional data configured by discrete image elements (for example, pixels in a two-dimensional image and voxels in a three-dimensional image). For example, an image may include medical images of an object acquired by an X-ray, a CT, an MRI, an ultrasound wave, and other medical image systems.

Also, in the present specification, an object may include a human being or an animal, or a part of the human being or the animal. For example, the object may include organs, such as the liver, the heart, the uterus, the brain, breasts, the abdomen, or blood vessels. Also, the "object" may include a phantom. The phantom denotes a material having a volume, a density, and an effective atomic number that is nearly equivalent to those of a living organism, and a phantom according to embodiments of the present invention may be a spherical phantom having similar properties to those of the human body.

In the present specification, a "user" is a medical expert, for example, a doctor, a nurse, a medical specialist, and a medical imaging expert, or an engineer managing medical apparatuses; however, the exemplary embodiments are not limited thereto.

An X-ray photographing apparatus is a medical imaging apparatus that acquires images of internal structures of the human body by transmitting an X-ray through the human body. The X-ray photographing apparatus may acquire medical images of a target object more simply within a shorter time than other medical imaging apparatuses including an MRI apparatus and a CT apparatus. Therefore, the X-ray system is widely used in a simple chest photographing, abdomen photographing, skeleton photographing, nasal sinuses photographing, neck soft tissue photographing, and breast photographing.

FIG. 1 is a block diagram of an X-ray photographing apparatus 100. The X-ray photographing apparatus 100 shown in FIG. 1 may be a fixed-type X-ray photographing apparatus or a moveable X-ray photographing apparatus.

Referring to FIG. 1, the X-ray photographing apparatus 100 includes a workstation 110, an X-ray irradiation unit 120, a high voltage generator 121, and a detector 130.

The workstation 110 includes an input unit 111 through which a user may input commands for manipulating the X-ray photographing apparatus 100 including an X-ray irradiation unit 120, and a control unit 112 controlling overall operations of the X-ray photographing apparatus 100. The workstation may further include a output unit 113 for outputting sounds indicating photographing-related information, such as X-ray irradiation.

The high voltage generator 121 generates a high voltage for generating X-rays, and applies the high voltage to an X-ray source 122.

The X-ray irradiation unit 120 includes the X-ray source 122 receiving the high voltage applied from the high voltage generator 121 to generate and irradiate the X-ray, and a collimator 123 for guiding a path of the X-ray irradiated from the X-ray source 122.

The detector 130 detects the X-ray that is irradiated from the X-ray irradiation unit 120 and transmitted through the object.

Also, the X-ray photographing apparatus 100 may further include a manipulation unit 140 including a sound output unit 141 outputting sound representing information relating to a photographing operation such as the X-ray irradiation under a control of the control unit 112.

The workstation 110, the X-ray irradiation unit 120, the high voltage generator 121, and the detector 130 may be connected to each other via wires or wirelessly. If they are connected to each other wirelessly, a device (not shown) for synchronizing clocks with each other may be further included.

The input unit 111 may include a keyboard, a mouse, a touch screen, a voice recognizer, a fingerprint recognizer, an iris recognizer, and the like that are well-known in the art. The user may input a command for irradiating the X-ray via the input unit 111, and to do this, the input unit 111 may include a switch for inputting the command. The switch may be configured so that an irradiation command for irradiating the X-ray may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-ray may be substantially input through the switch. When the user manipulates the switch as described above, the input unit 111 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 111, the high voltage generator 121 starts a pre-heating operation, and when the pre-heating is finished, the high voltage generator 121 outputs a ready signal to the control unit 112. In addition, the detector 130 also needs to prepare for detecting the X-ray, and thus, when the high voltage generator 121 receives the prepare signal output from the input unit 111, the high voltage generator 121 outputs a prepare signal to the detector 130 at the same time of performing the pre-heating operation, so that the detector 130 may prepare for detecting the X-ray transmitted through the object. The detector 130 prepares for detecting the X-ray when receiving the prepare signal, and when the preparing for the detection is finished, the detector 130 outputs a ready signal to the high voltage generator 121 and the control unit 112.

When the pre-heating operation of the high voltage generator 121 is finished, the detector 130 is ready for the detecting the X-ray, and the irradiation signal is output from the input unit 111 to the high voltage generator 121, the high voltage generator 121 generates and applies the high voltage to the X-ray source 122, and the X-ray source 122 irradiates the X-ray.

When the irradiation signal is output from the input unit 111, the control unit 112 may output a sound output signal to the sound output unit 141 so that the sound output unit 141 outputs a predetermined sound and the object may recognize the irradiation of X-ray. Also, the sound output unit 141 may output sound representing other information relating to the photographing, in addition to the X-ray irradiation. In FIG. 1, the sound output unit 141 is included in the manipulation unit 140; however, the exemplary embodiments are not limited thereto, and the sound output unit 141 may be located at a different location from the manipulation unit 140. For example, the sound output unit 141 may be included in the workstation 110, or may be located on a wall surface of an examination room in which the X-ray photographing of the object is performed.

The control unit 112 controls locations of the X-ray irradiation unit 120 and the detector 130, a photographing timing, and photographing conditions according to photographing conditions set by the user.

In more detail, the control unit 112 controls the high voltage generator 121 and the detector 130 according to the command input via the input unit 111 so as to control an irradiation timing of the X-ray, an intensity of the X-ray, and an irradiation region of the X-ray. Also, the control unit 112 adjusts the location of the detector 130 according to a predetermined photographing condition, and controls an operation timing of the detector 130.

In addition, the control unit 112 generates a medical image of the object by using image data transmitted from the detector 130. In particular, the control unit 112 receives the image data from the detector 130, and then, generates the medical image of the object by removing noise in the image data, and adjusting a dynamic range and interleaving of the image data.

The X-ray photographing apparatus 100 shown in FIG. 1 may further include an output unit (not shown) for outputting the medical image generated by the control unit 112. The output unit may output information that is necessary for the user to manipulate the X-ray photographing apparatus 100, for example, a user interface (UI), user information, or object information. The output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices well known in the art.

The workstation 110 shown in FIG. 1 may further include a communication unit (not shown) that may be connected to a server 162, a medical apparatus 164, and a portable terminal 166 via a network 160.

The communication unit may be connected to the network 160 via wires or wirelessly to communicate with the external server 162, the external medical apparatus 164, or the external portable terminal 166. The communication unit may transmit or receive data relating to diagnosis of the object via the network 160, and may transmit or receive medical images captured by the other medical apparatus 164, for example, a CT, an MRI, or an X-ray photographing apparatus. Moreover, the communication unit may receive a medical history or treatment schedule of an object (e.g., a patient) from the server 162 to diagnose a disease of the object. Also, the communication unit may perform data communication with the portable terminal 166 such as a mobile phone of a doctor or a patient, a personal digital assistant (PDA), or a laptop computer, as well as the server 162 or the medical apparatus 164 in a hospital.

The communication unit may include one or more elements enabling to communicate with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the embodiments of the present invention are not limited thereto.

The wired communication module is a module for communicating by using an electric signal or an optical signal, and the wired communication technology may be wired communication technology using a pair cable, a coaxial cable, or an optical fiber cable, and a wired communication technology that is well known in the art.

The wireless communication module may transmit/receive a wireless signal to/from at least one of a base, an external device, and a server in a mobile communication network. Here, the wireless signal may be a voice call signal, a video call signal, or various types of data according to text/multimedia messages transmission.

The X-ray photographing apparatus 100 shown in FIG. 1 may include a plurality of digital signal processors (DSPs), an ultra-small calculator, and a processing circuit for specialized usage (for example, for high speed analog/digital (A/D) conversion, high speed Fourier transformation, an array process, etc.).

In addition, the communication between the workstation 110 and the X-ray irradiation unit 120, the workstation 110 and the high voltage generator 121, and the workstation 110 and the detector 130 may use a high speed digital interface, such as low voltage differential signalling (LVDS), asynchronous serial communication, such as universal asynchronous receiver transmitter (UART), synchronous serial communication, or a low latency network protocol, such as a controller area network (CAN), and other various communication methods that are well known in the art may be used.

Figure 2:
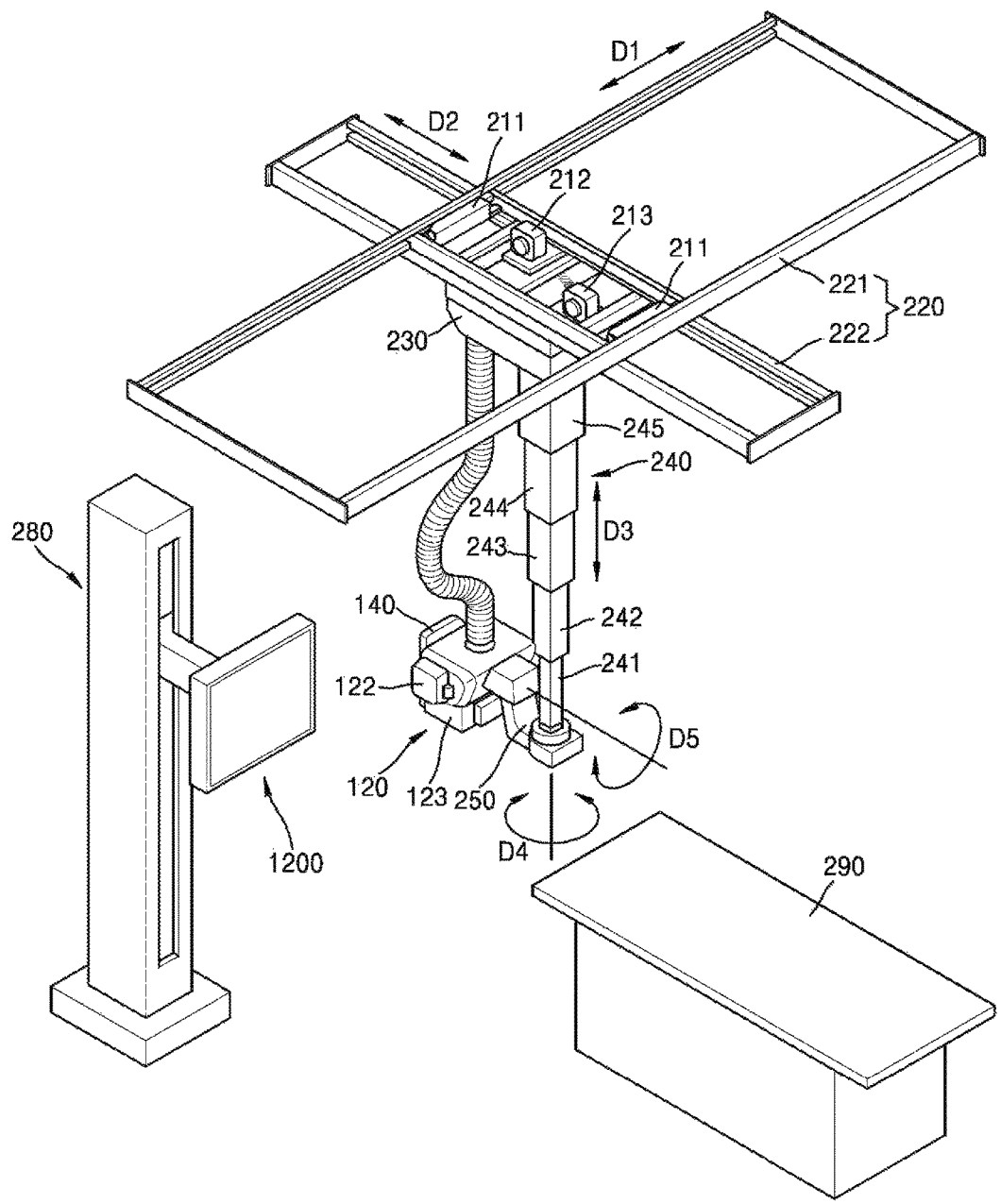
FIG. 2 is a perspective view of a fixed type X-ray photographing apparatus according to an exemplary embodiment.

FIG. 2 is a perspective view of a fixed type X-ray photographing apparatus 200.

As shown in FIG. 2, the X-ray photographing apparatus 200 includes a manipulation unit 140 for providing a user with an interface for manipulating the X-ray photographing apparatus 200, an X-ray irradiation unit 120 irradiating the X-ray to an object, a detector 130 detecting the X-ray that has passed through the object, first through third motors 211, 212, and 213 providing a driving power to transport the X-ray irradiation unit 120, a guide rail 220, a moving carriage 230, and a post frame 240 formed to transport the X-ray irradiation unit 120 by using the driving power of the motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other.

The first guide rail 221 is provided on a ceiling of the examination room in which the X-ray photographing apparatus 200 is provided.

The second guide rail 222 is located under the first guide rail 221, and is mounted to the first guide rail 221 so as to slide along the first guide rail 221. A roller (not shown) that may move along the first guide rail 221 may be provided on the first guide rail 221. The second guide rail 222 is connected to the roller (not shown) to move along the first guide rail 221.

A first direction D1 is defined as a direction in which the first guide rail 221 is extended, and a second direction D2 is defined as a direction in which the second guide rail 222 is extended. Therefore, the first direction D1 and the second direction D2 cross each other, and may be parallel to the ceiling of the examination room.

The moving carriage 230 is provided under the second guide rail 222 so as to move along the second guide rail 222. A roller (not shown) moving along the second guide rail 222 may be provided on the moving carriage 230.

Therefore, the moving carriage 230 may move in the first direction D1 with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in an up and down direction of the examination room in a state of being fixed to the moving carriage 230.

A third direction D3 is defined as a direction in which the length of the post frame 240 is increased or reduced. Therefore, the third direction D3 may cross the first direction D1 and the second direction D2.

The X-ray irradiation unit 120 may include an X-ray source 122 generating the X-ray, and a collimator 123 adjusting an irradiation region of the X-ray that is generated and irradiated from the X-ray source 122. The X-ray source 122 includes an X-ray tube that may be realized as a diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of 3 to 5 A may be applied to an electric wire connected to the filament to heat the filament.

In addition, when a high voltage of about 10 to about 300 kvp is applied between the cathode and the anode, the thermal electrons are accelerated to crash onto a target material of the cathode, and then, an X-ray is generated. The X-ray is irradiated to an external region via a window, and the window may be formed as a beryllium thin film. Here, most of the energy of the electrons colliding with the target material is consumed as heat, and remaining energy is converted into the X-ray.

The cathode is mainly formed of copper, and the target material is provided at an opposite side to the anode. The target material may be a high resistive material such as Cr, Fe, Co, Ni, W, or Mo. The target material may be rotated by a rotating field. When the target material is rotated, an electron impact area is increased, and a heat accumulation rate per unit area may be increased ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kvp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, a dose of the X-ray (the number of X-ray photons) generated when the thermal electrons collide with the target material is increased.

Therefore, the energy of the X-ray may be adjusted according to the tube voltage, and the intensity or dose of the X-ray may be adjusted according to the tube current and the X-ray exposure time.

The high voltage generator 121 may be provided in the X-ray source 122; however, the exemplary embodiments are not limited thereto, and the high voltage generator 121 may be provided on another portion of the X-ray photographing apparatus 200.

The detector 130 is a detector for detecting the X-ray that has passed through the object, and may be realized as a table type 290 or a stand type 280. The detector 130 may be formed by using a thin film transistor (TFT) or a charge coupled device (CCD).

A rotating joint 250 is provided between the X-ray irradiation unit 120 and the post frame 240. The rotating joint 250 allows the X-ray irradiation unit 120 to be coupled to the post frame 240, and supports a load applied to the X-ray irradiation unit 120.

The X-ray irradiation unit 120 connected to the rotating joint 250 may rotate on a plane that is perpendicular to the third direction D3. Here, a rotating direction of the X-ray irradiation unit 120 may be defined as a fourth direction D4.

Also, the X-ray irradiation unit 120 may be configured to be rotatable on a plane perpendicular to the ceiling of the examination room. Therefore, the X-ray irradiation unit 120 may rotate in a fifth direction D5 that is a rotating direction based on an axis that is in parallel with the first direction D1 or the second direction D2, with respect to the rotating joint 250.

The motors 211, 212, and 213 may be provided to move the X-ray irradiation unit 120 in the first through third directions D1, D2, and D3. The motors 211, 212, and 213 may be electrically driven, and the motors 211, 212, and 213 may respectively include an encoder.

The motors 211, 212, and 213 may be provided on various locations in consideration of design convenience. For example, the first motor 211 moving the second guide rail 222 in the first direction D1 may be provided around the first guide rail 221, the second motor 212 for moving the moving carriage 230 in the second direction D2 may be provided around the second guide rail 222, and the third motor 213 increasing or reducing the length of the post frame 240 in the third direction D3 may be provided in the moving carriage 230. In another example, the first through third motors 211, 212, and 213 may be connected to a driving power transfer unit (not shown) so as to linearly move the X-ray irradiation unit 120 in the first through third directions D1, D2, and D3. The driving power transfer unit (not shown) may be a belt and a pulley, a chain and a sprocket, a shaft, or the like.

As another example, motors may be provided between the rotating joint 250 and the post frame 240 and between the rotating joint 250 and the X-ray irradiation unit 120 in order to rotate the X-ray irradiation unit 120 in the fourth direction D4 and the fifth direction D5.

The manipulation unit 140 for providing the user with the interface for inputting various information about the X-ray photographing and manipulating each device may be provided at a side surface of the X-ray irradiation unit 120. The interface may include input unit 142.

Although FIG. 2 shows the fixed type X-ray photographing apparatus 200 connected to the ceiling of the examination room, the X-ray photographing apparatus 200 of FIG. 2 is an example for convenience of comprehension. That is, the X-ray photographing apparatus according to the exemplary embodiments may be an X-ray photographing apparatus having various structures, for example, a C-arm-type X-ray photographing apparatus and an angiography X-ray photographing apparatus.

Figure 3:
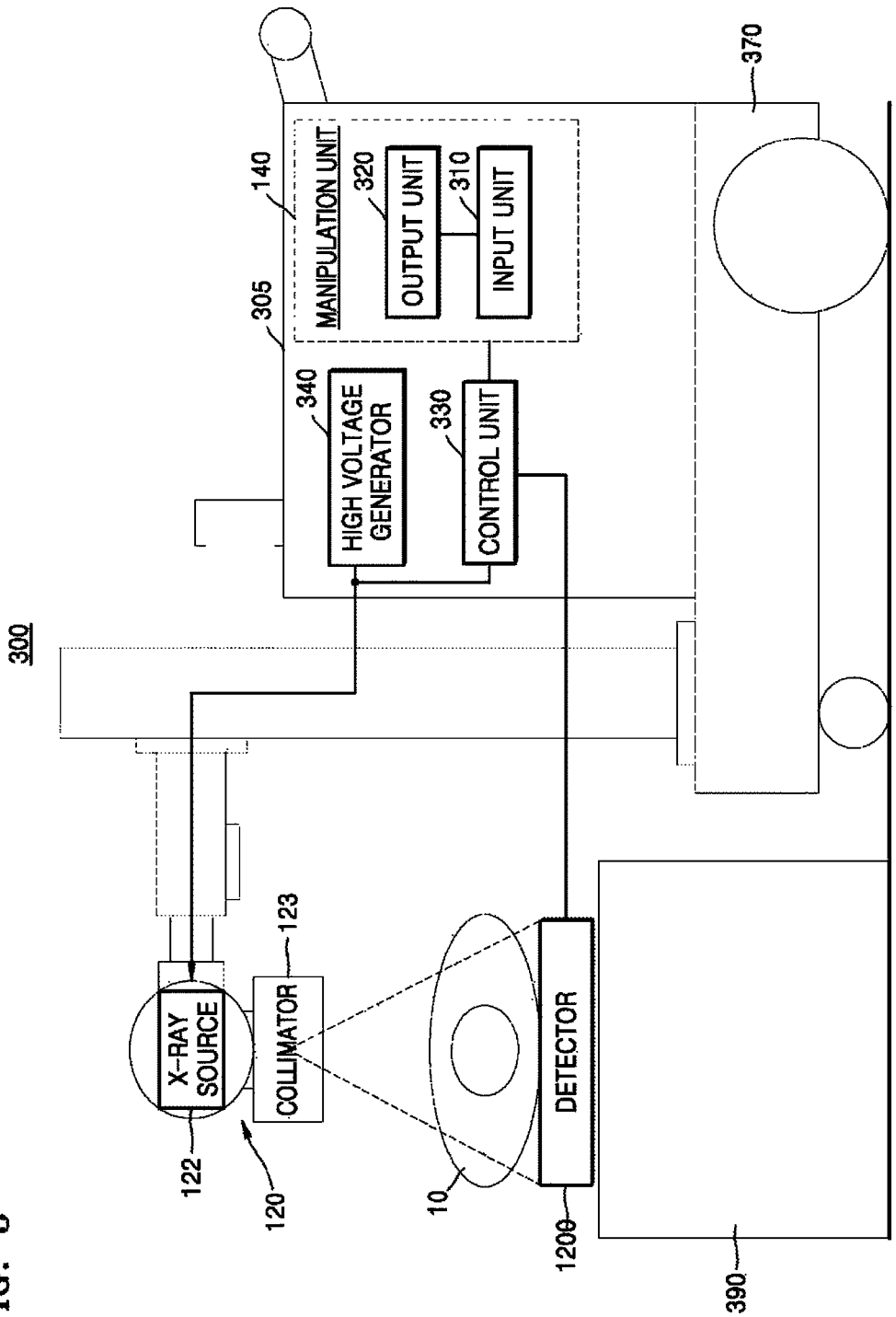
FIG. 3 illustrates a mobile X-ray photographing apparatus according to an exemplary embodiment, the mobile X-ray photographing apparatus capable of performing an X-ray photographing operation regardless of photographing locations.

FIG. 3 illustrates a mobile X-ray photographing apparatus 300 according to an exemplary embodiment, the mobile X-ray photographing apparatus 300 capable of performing an X-ray photographing operation regardless of photographing locations.

The mobile X-ray photographing apparatus 300 shown in FIG. 3 includes a moving unit 370 including wheels for moving the mobile X-ray photographing apparatus 300, an input unit 310 for receiving inputs for operating the mobile X-ray photographing apparatus 300, a high voltage generating unit 340 for generating a high voltage applied to the X-ray source 122, a sound output unit 320 for outputting sounds indicating photographing-related information, such as X-ray irradiation, a main unit 305 including a control unit 330 for controlling overall operations of the mobile X-ray photographing apparatus 300, an X-ray irradiation unit 120 that includes an X-ray source 122 for generating an X-ray and a collimator 357 for guiding a path for an X-ray, and a detector 1200 for detecting an X-ray that is irradiated by the X-ray irradiation unit 120 and is transmitted through a target object 10 on table top 390.

The input unit 310 receives a certain input from a user. The input unit 310 may include a keyboard, a mouse, a touch screen, a voice recognizer, a fingerprint recognizer, an iris recognizer, and one or more various other input units that will be obvious to one of ordinary skill in the art. A user may input a command for X-ray irradiation via the input unit 310, where one or more switches for inputting such a command may be arranged at the input unit 310. The switch may be arranged to be pressed in two stages to input a command for X-ray irradiation.

In other words, when a user presses the switch, the switch may input a preparation command for instructing warm-up for X-ray irradiation and, when the user further presses the switch, the switch may input an irradiation command for instructing actual X-ray irradiation. When the user operates the switch as described above, the input unit 310 generates signals corresponding to a command input based on the operation of the switch, that is, a preparation signal and an irradiation signal and outputs the preparation signal and the irradiation signal to the high voltage generating unit 340 that generates a high voltage for X-ray irradiation.

The high voltage generating unit 340 receives a preparation signal output by the input unit 310 and starts warm-up. When the warm-up is completed, the high voltage generating unit 340 outputs a signal indicating that the preparation is complete to the control unit 330. Furthermore, to detect an X-ray, it is also necessary for the detector 1200 to prepare for X-ray detection. When the high voltage generating unit 340 receives the preparation signal output by the input unit 310, the high voltage generating unit 340 starts warm-up and outputs a preparation signal to the detector 1200, such that the detector 1200 prepares to detect an X-ray transmitted through a target object 10. When the detector 1200 receives the preparation signal, the detector 1200 starts preparation to detect an X-ray. When the preparation is complete, the detector 1200 outputs a signal indicating that the preparation for X-ray detection is completed to the high voltage generating unit 340 and the control unit 330.

When the high voltage generating unit 340 is warmed up, the detector 1200 is prepared to detect an X-ray, and the input unit 310 outputs an irradiation signal to the high voltage generating unit 340, the high voltage generating unit 340 generates a high voltage and applies the high voltage to the X-ray source 122, and the X-ray source 122 irradiates an X-ray. When the irradiation signal is output by the input unit 310, the control unit 330 may output a sound output signal to the sound output unit 320 to output a certain sound via the sound output unit 320 to notify X-ray irradiation to a target object 10. Furthermore, the sound output unit 320 may also output sounds indicating other photographing-related information other than X-ray irradiation.

Although FIG. 3 shows that the sound output unit 320 is included in the main unit 305, the exemplary embodiments is not limited thereto. For example, the sound output unit 320 may be located at a location external to the mobile X-ray photographing apparatus 300, e.g., on a wall of a hospital room.

The control unit 330 controls locations of the X-ray irradiation unit 120 and the detector 1200, a photographing timing, and photographing conditions according to photographing conditions set by the user.

Furthermore, the control unit 330 generates a medical image regarding a target object 10 by using image data received from the detector 1200. In detail, the control unit 330 may generate a medical image regarding a target object 10 by receiving image data from the detector 1200, removing noises in the image data, and adjusting dynamic range and interleaving.

The main unit 305 of the mobile X-ray photographing apparatus 300 shown in FIG. 3 may further include an output unit (not shown) that outputs a medical image generated by the control unit 330. The output unit may output a user interface (UI), user information or target object information, or other information needed for a user to operate the mobile X-ray photographing apparatus 300.

Figure 4:
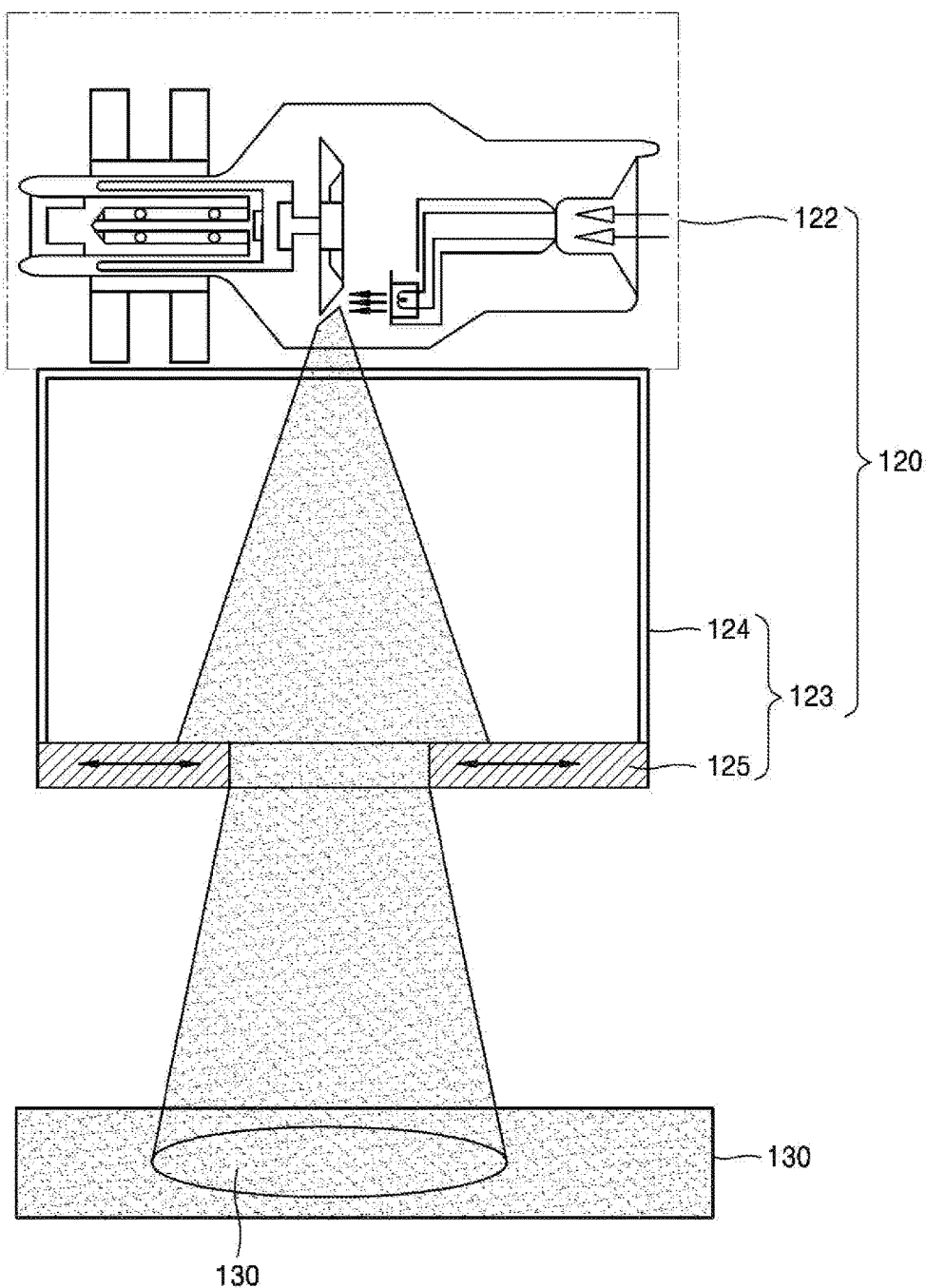
FIG. 4 is a diagram showing an X-ray irradiation field of a collimator of a common X-ray photographing apparatus.

FIG. 4 is a diagram showing an X-ray irradiation field 170 of a collimator 123 of a common X-ray photographing apparatus.

The collimator 123 of a common X-ray photographing apparatus may include a housing 124 that forms a certain space therein and an irradiation field area adjusting unit 125 arranged at a front side of the housing 124.

The irradiation field area adjusting unit 125 is arranged at a lower portion of the housing 124 and may be moved in horizontal directions as a driving unit (not shown) is driven. In other words, an X-ray irradiation field may be adjusted by controlling an interval of the driving unit. For example, as shown in FIG. 4, a portion where an X-ray intersects a light receiving surface of the detector 130 is referred to as the X-ray irradiation field 170, where an area of irradiation of an X-ray may be determined based on an opening of an aperture arranged in the X-ray irradiation unit 120.

Furthermore, to control opening of the aperture, a technique for precisely controlling opening of the aperture by arranging gears around the aperture is applied, where an area of irradiation of an X-ray is controlled by opening or closing the aperture by operating the gears.

However, since a user manually controls the X-ray irradiation field 170 of an X-ray irradiated by the collimator 123, precision is deteriorated and it takes an excessive time period for checking a precise point of irradiation.

Figure 5:
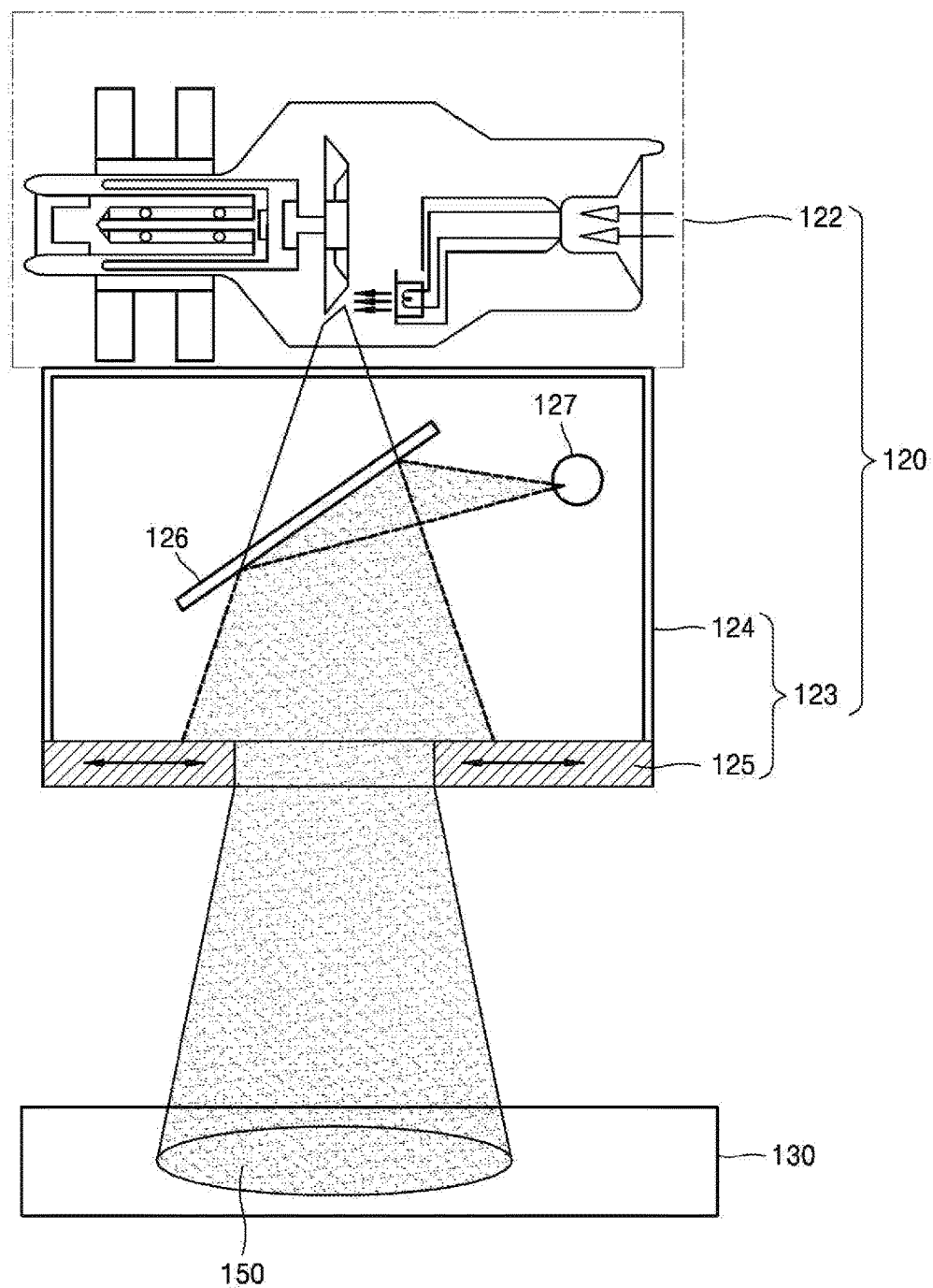
FIG. 5 is a diagram showing a light irradiation field of the collimator of a common X-ray photographing apparatus.

FIG. 5 is a diagram showing a light irradiation field 150 of the collimator 123 of a common X-ray photographing apparatus.

As described above with reference to FIG. 4, it is necessary for the collimator 123, which determines an area of X-ray irradiation or the X-ray irradiation field 170 during its operation, to check a precise point of X-ray irradiation.

In relation thereto, the collimator 123 may include a point light source 127 for generating a visible ray that may be recognized by a user and a reflection mirror 126 for reflecting a visible ray generated by the point light source 127 and irradiating the reflected visible ray to a target object 10.

Therefore, a user may visibly recognize a target object to be photographed as a visible ray generated by the point light source 127 and reflected by the reflection mirror 126 that is arranged tilted behind the collimator 123

For example, as shown in FIG. 5, an area at which a visible ray irradiated by the irradiation field area adjusting unit 125 intersects with the light receiving surface of the detector 130 may be referred to as the light irradiation field 150, where the light irradiation field 150 may vary according to a location and/or a tilted angle of the reflection mirror 126 or a location of the point light source 127. The more the X-ray irradiation field 170 matches the light irradiation field 150, the more precisely an X-ray may be irradiated to a target object.

Furthermore, a cross-like indicator may be included to indicate the center of an X-ray source as information regarding a visible ray in the light irradiation field 150, where the visible ray is generated by the point light source 127. For example, a cross-like indicator may be generated by forming a non-transparent portion in a transparent material. However, in this case, the indicator is always fixed. Therefore, when the center of an X-ray source is dislocated based on external factors, it is necessary for a skilled technician to manually mechanically re-adjust the X-ray source.

Furthermore, a visible ray generated by the point light source 127 only includes a cross-like indicator for indicating the center of an X-ray source and is unable to provide information regarding a target object or information related to an X-ray photographing operation to a user.

Figure 6:
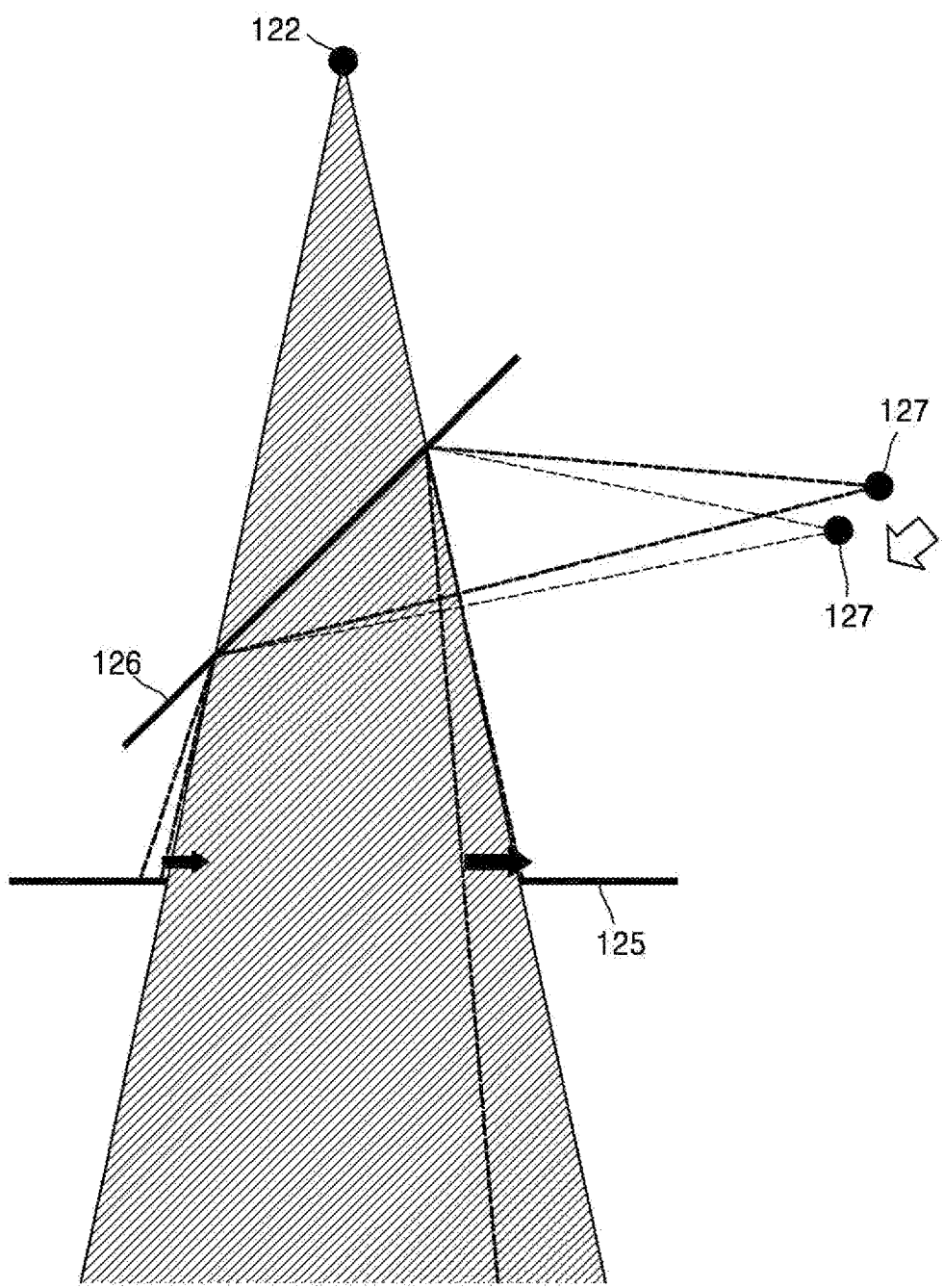
FIG. 6 is a diagram showing that the X-ray irradiation field matches the light irradiation field in the collimator of an X-ray photographing apparatus.

FIG. 6 is a diagram showing that the X-ray irradiation field 170 matches the light irradiation field 150 in the collimator 123 of an X-ray photographing apparatus.

Generally, it may be determined that an X-ray irradiation field matches a light irradiation field when a distance between the center of the X-ray irradiation field and the center of the light irradiation field is within 2% of a distance SID between an X-ray focus and a light receiving surface.

If there is significant inconsistency between an X-ray irradiation field and a light irradiation field, it is likely that an X-ray is not irradiated to a portion of a target object to be photographed, and thus it may likely be necessary to irradiate an X-ray to the target object again. In this case, due to a repetition of X-ray photographing operations, the target object may suffer an X-ray overdose.

Therefore, it is necessary for an X-ray photographing apparatus to be capable of determining whether an X-ray irradiation field matches a light irradiation field and adjust the X-ray irradiation field and the light irradiation field to match each other if the X-ray irradiation field does not match the light irradiation field.

For example, if a path in which an X-ray is irradiated and a path in which a visible ray travels are identical or similar to each other, it may be determined that an X-ray irradiation field matches a light irradiation field, and a user may easily recognize an area of irradiation to which an X-ray is actually irradiated.

Meanwhile, a path in which a visible ray generated by the point light source 127 travels may be changed based on a location and/or a tilted angle of the reflection mirror 126 or a location of the point light source 127.

Therefore, as shown in FIG. 6, if a location of the point light source 127 is changed based on external factors, a light irradiation field and an X-ray irradiation field may not match each other. In this case, to match the light irradiation field to the X-ray irradiation field, it is necessary to precisely adjust a location of the point light source 127 by using a mechanical adjusting unit including 3 or more axes as shown in FIG. 6 to match the light irradiation field to the X-ray irradiation field.

In this case, it is necessary to precisely adjust a location of the reflection mirror 126 or the point light source 127 by the hands of a skilled technician, where it is necessary to mechanically disassemble and assemble a collimator repeatedly.

Therefore, if a location of the reflection mirror 126 or the point light source 127 is changed based on external factors, mechanical repair is necessary, which takes a long time period.

Figure 7:
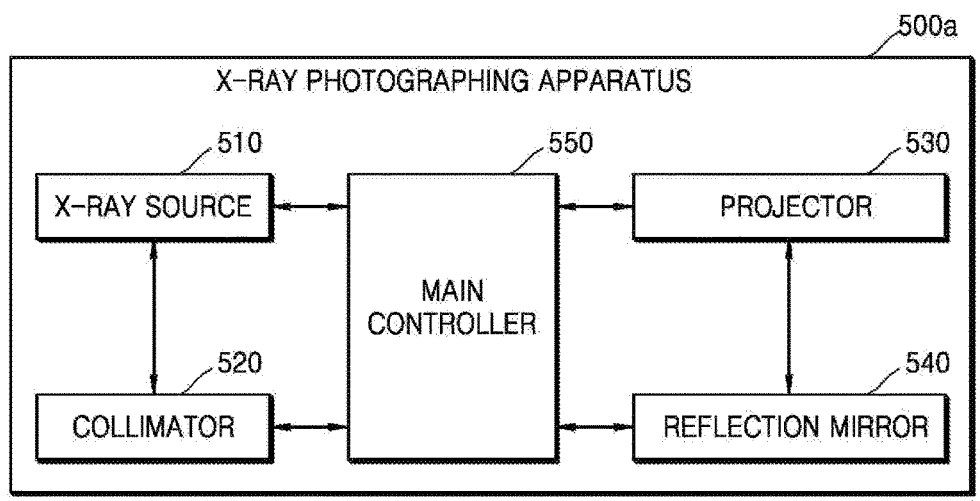
FIG. 7 is a block diagram of an X-ray photographing apparatus according to an exemplary embodiment.

FIG. 7 is a block diagram of an X-ray photographing apparatus 500*a* according to an exemplary embodiment.

The X-ray photographing apparatus 500*a* according to an exemplary embodiment may include an X-ray source 510, a collimator 520, a projector 530, a reflection mirror 540, and a main controller 550.

If the X-ray system 1000 of FIG. 1 includes the X-ray photographing apparatus 500*a* of FIG. 7, the X-ray photographing apparatus 500*a* of FIG. 7 may be identical to the X-ray photographing apparatus of FIG. 1. In detail, the X-ray source 510, the collimator 520, and the main controller 550 of the X-ray photographing apparatus 500*a* of FIG. 7 may be identical to the X-ray source 122, the collimator 123, and the control unit 115 of the X-ray photographing apparatus 100 of FIG. 1. Therefore, descriptions thereof given above with reference to FIG. 1 will be omitted.

Hereinafter, the above-stated components will be described below.

The X-ray source 510 according to an exemplary embodiment may generate and irradiate an X-ray.

For example, the X-ray source 510 may generate and irradiate a focused X-ray.

The collimator 520 according to an exemplary embodiment may adjust an irradiation field of an X-ray irradiated by the X-ray source 510.

The projector 530 according to an exemplary embodiment may generate a visible ray image by using image signals and project the visible ray image.

An image signal according to an exemplary embodiment may be an image signal received from an external source via the main controller 550.

In this case, a visible ray image corresponding to a light irradiation field may refer to a multi-dimensional data consisting of discrete image elements (e.g., pixels in a 2-dimensional image and voxels in a 3-dimensional image) including characters or pictures generated based on image signals received from an external source.

For example, if an image signal includes information regarding a photographing operation of an X-ray photographing apparatus or information regarding a target object to be photographed by the X-ray photographing apparatus, a visible ray image projected by the projector 530 may include not only information regarding an area of X-ray irradiation, but also the information regarding the photographing operation of the X-ray photographing apparatus or the information regarding the target object to be photographed by the X-ray photographing apparatus.

Therefore, based on a visible ray image corresponding to a light irradiation field, a user may recognize information other than the information regarding the area of X-ray irradiation, e.g., information regarding a target object or information regarding an X-ray photographing operation.

Detailed descriptions thereof will be given below with reference to FIGS. 11 through 14.

Furthermore, a visible ray image corresponding to a light irradiation field may be determined based on a size of a visible ray image projected by a projection unit or a location of a visible ray image projected by the projection unit.

The reflection mirror 540 according to an exemplary embodiment may project a visible ray image projected by the projector 530 to an X-ray photographing area.

For example, the reflection mirror 540 may project a visible ray image projected by the projector 530 to an X-ray photographing area, where a location of the visible ray image projected onto a light receiving surface may vary based on a location of the reflection mirror 540.

The main controller 550 according to an exemplary embodiment may control the projector 530 to match a light irradiation field corresponding to the visible ray image projected to the X-ray photographing area to an X-ray irradiation field.

For example, the main controller 550 of the X-ray photographing apparatus may determine whether the X-ray irradiation field matches the visible ray image corresponding to the light irradiation field and transmit a signal to a projector controller 620 to match the X-ray irradiation field to the light irradiation field.

In this case, based on the signal received from the main controller 550, the projector controller 620 may change a location and/or size of the visible ray image projected by the projector.

Furthermore, the projector controller 620 may change a focus of the visible ray image corresponding to the light irradiation field, thereby providing a focused visible ray image to a user.

Figure 8:
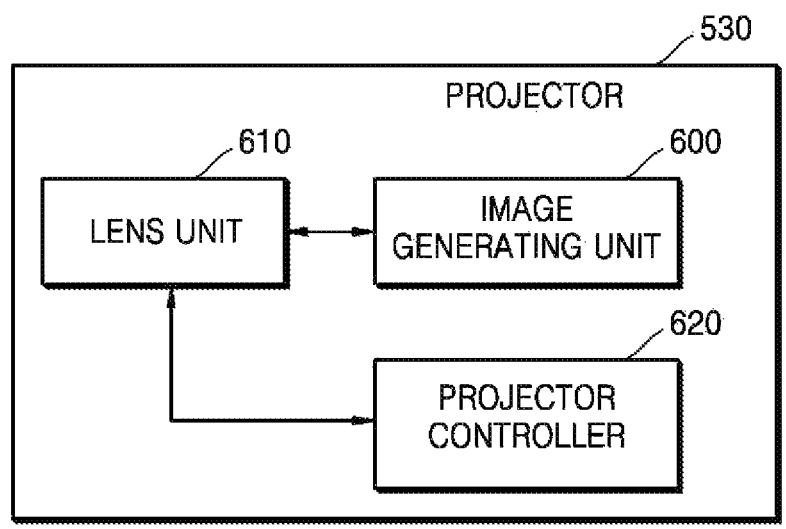
FIG. 8 is a block diagram of the projector according to an exemplary embodiment.

FIG. 8 is a block diagram of the projector 530 according to an exemplary embodiment.

As shown in FIG. 8, the projector 530 according to an exemplary embodiment may further include an image generating unit 600, a lens unit 610, and the projector controller 620.

The image generating unit 600 according to an exemplary embodiment may generate a visible ray image by using image signals.

A visible ray image according to an exemplary embodiment may refer to a multi-dimensional data consisting of discrete image elements (e.g., pixels in a 2-dimensional image and voxels in a 3-dimensional image) including characters or pictures generated based on image signals received from an external source.

For example, a visible ray image generated by the image generating unit 600 may include not only information regarding an area of X-ray irradiation, but also information regarding a photographing operation of an X-ray photographing apparatus or information regarding a target object to be photographed by the X-ray photographing apparatus.

Therefore, based on a visible ray image corresponding to a light irradiation field, a user may recognize information other than the information regarding the area of X-ray irradiation, e.g., the information regarding the target object or the information regarding the X-ray photographing operation.

The image generating unit 600 according to an exemplary embodiment may further include a display device 605, a light source 601, and a filter 603. Detailed descriptions thereof will be given below with reference to FIG. 9.

The lens unit 610 according to an exemplary embodiment consists of a plurality of lenses and is capable of focusing a visible ray image generated by the image generating unit 600.

For example, the lens unit 610 includes a zoom lens for widening or narrowing a field of view based on focal lengths and a focus lens for focusing on an object, where each of such lenses may be a single lens or a group of a plurality of lenses.

In this case, optical information regarding size or focus of a visible ray image irradiated from the lens unit 610 to the reflection mirror 540 may vary according to focal lengths of the lens unit 610.

The projector controller 620 according to an exemplary embodiment may control at least one or more of the X-ray photographing apparatus 100 and the lens unit 610.

In this case, the projector controller 620 may match a visible ray image corresponding to a light irradiation field to an X-ray irradiation field by controlling the image generating unit 600 and/or the lens unit 610.

For example, to match the visible ray image corresponding to the light irradiation field to the X-ray irradiation field, location of the visible ray image projected by the projector 530 and/or size of the visible ray image projected by the projector 530 may be adjusted.

For example, the projector controller 620 may adjust location of the visible ray image projected by the projector 530 by controlling the image generating unit 600 included in the projector 530.

For example, the projector controller 620 may adjust location of the visible ray image projected by the projector 530 by adjusting location of an active area of the display device 605 used for generating the visible ray image, thereby matching location of the light irradiation field to location of the X-ray irradiation field. Detailed descriptions thereof will be given below with reference to FIGS. 15 and 16.

Furthermore, the projector controller 620 may control size and/or focus of the visible ray image projected by the projector 530 by controlling the lens unit 610 included in the projector 530.

For example, the projector controller 620 may adjust a focal length by adjusting locations of one or more of a plurality of lenses included in the lens unit 610 and perform operations including auto-focusing, zooming in/out, and focus changing.

In other words, the projector controller 620 may adjust a focal length by adjusting locations of one or more of a plurality of lenses, thereby adjusting a size of the visible ray image projected by the projector 530.

Therefore, the projector controller 620 may match size of the light irradiation field to size of the X-ray irradiation field by adjusting size of the visible ray image projected by the projector 530.

Furthermore, the projector controller 620 may adjust focus of the visible ray image projected by the projector 530 by controlling locations of one or more of a plurality of lenses.

Detailed descriptions thereof will be given below with reference to FIG. 17.

Figure 9:
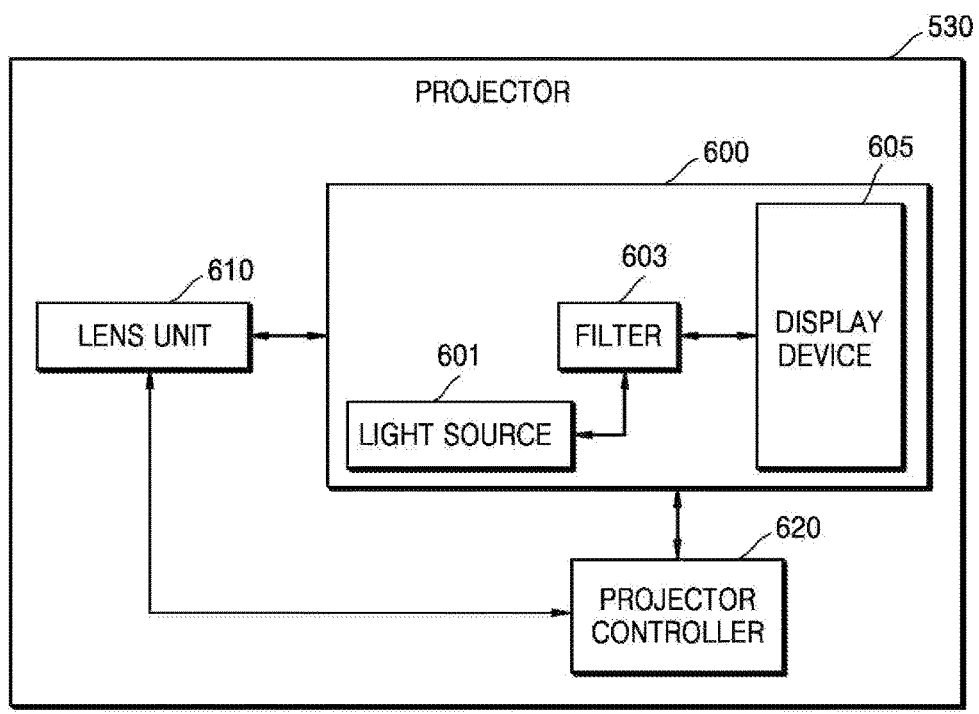
FIG. 9 is a block diagram of the image generating unit according to an exemplary embodiment.

FIG. 9 is a block diagram of the image generating unit 600 according to an exemplary embodiment.

As shown in FIG. 8, the image generating unit 600 according to an exemplary embodiment may further include the light source 601, the filter 603, and the display device 605.

The display device 605 may convert image signals to a projection image.

For example, a group of pixels used to convert image signals to a projection image in the display device 605 may be referred to as an active area, where an active area in the display device 605 may be determined by the projector controller 620. For example, location of an active area in the display device 605 may be adjusted by the projector controller 620 based on signals generated based on a consistency between a light irradiation field and an X-ray irradiation field determined by the main controller 550.

In this case, if a location of the active area of the display device 605 is adjusted, a location of a visible ray image projected by the projector 530 may be adjusted, and thus a visible ray image, which corresponds to a light irradiation field and is projected onto a light receiving surface, may also be adjusted.

In other words, the projector controller 620 may match a location of a visible ray image corresponding to the light irradiation field to a location of the X-ray irradiation field by adjusting location of the active area of the display device 605.

For example, the display device 605 may include display devices including a deformable mirror device (DMD), a liquid crystal on silicon (LCoS), and an organic light emitting diode (OLED). In this case, various methods of converting image signals to a projection image are known in the art, such as a learning-based method, and thus a method of converting image signals to a projection image is not limited to a particular method.

Detailed descriptions thereof will be given below with reference to FIGS. 15 and 16.

Furthermore, if the display device 605 is a DMD, an X-ray photographing apparatus 500*a*, 500*b*, or 500*c* according to an exemplary embodiment may have a similar operation mechanism as that of a digital light processing (DLP) type projector and may generate and project a visible ray image via the projector 530. In this case, the display device 605 of the X-ray photographing apparatus 500*a*, 500*b*, or 500*c* may employ a digital micro-mirror device (DMD), which is a semiconductor optical switch including micromirrors integrated therein.

For example, a micro-mirror arranged at each pixel of the display device 605 may be tilted at an angle from −10 degrees to +10 degrees. Detailed descriptions thereof will be given below with reference to FIGS. 25 through 27.

The light source 601 according to an exemplary embodiment may provide a light for generating a projection image, which is an image converted by the display device 605, as a visible ray image. For example, a light source 601 may be a lamp arranged inside the housing of a projector 530.

Furthermore, the filter 603 according to an exemplary embodiment refers to red (R), green (G), and blue (B) filters arranged between the light source 601 and the display device 605, whereby various combinations of colors may be embodied by filtering a light provided by the light source 601 and irradiating the filtered light to the display device 605.

Figure 10:
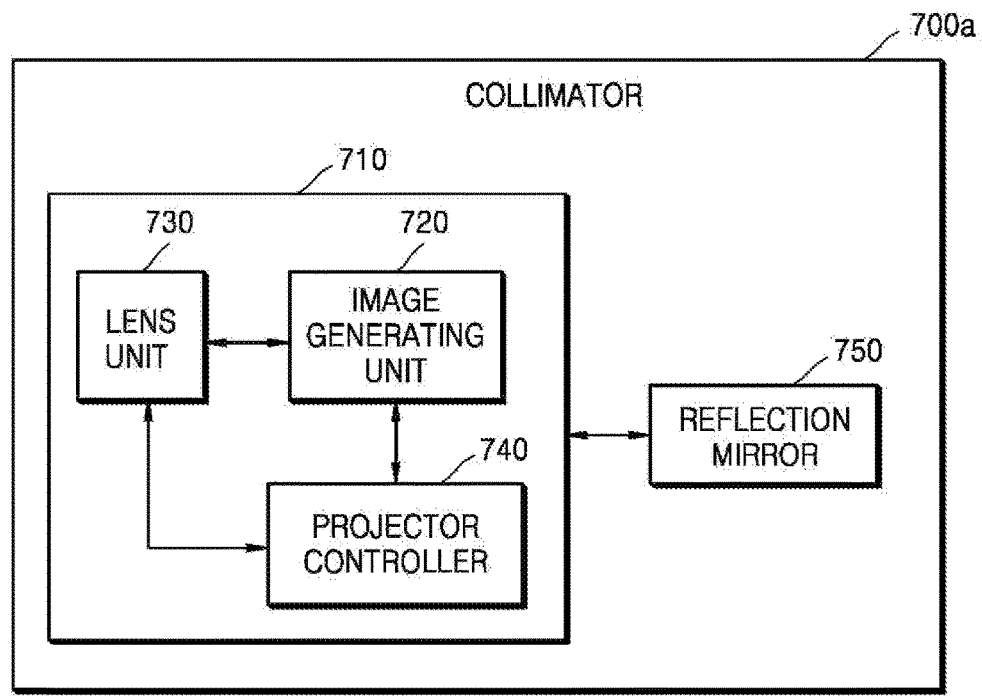
FIG. 10 is a block diagram of a collimator including a projector according to an exemplary embodiment.

FIG. 10 is a block diagram of a collimator 700*a* including a projector 710 according to an exemplary embodiment.

As shown in FIG. 10, the collimator 700*a* according to an exemplary embodiment may include the projector 710, which includes an image generating unit 720, a lens unit 730, and a projector controller 740, and a reflection mirror 750.

If the collimator 700*a* of FIG. 10 is included in the X-ray photographing apparatus 500*a* of FIG. 7, the projector 710 and the reflection mirror 750 of FIG. 10 may be identical to the projector 530 and the reflection mirror 540 of FIG. 7, respectively. In detail, the image generating unit 720, the lens unit 730, and the projector controller 740 of FIG. 10 may be identical to the image generating unit 600, the lens unit 610, and the projector controller 620 of FIG. X-ray photographing apparatus 500*a* of FIG. 8, respectively. Therefore, descriptions thereof given above with reference to FIG. 8 will be omitted.

Figure 11:
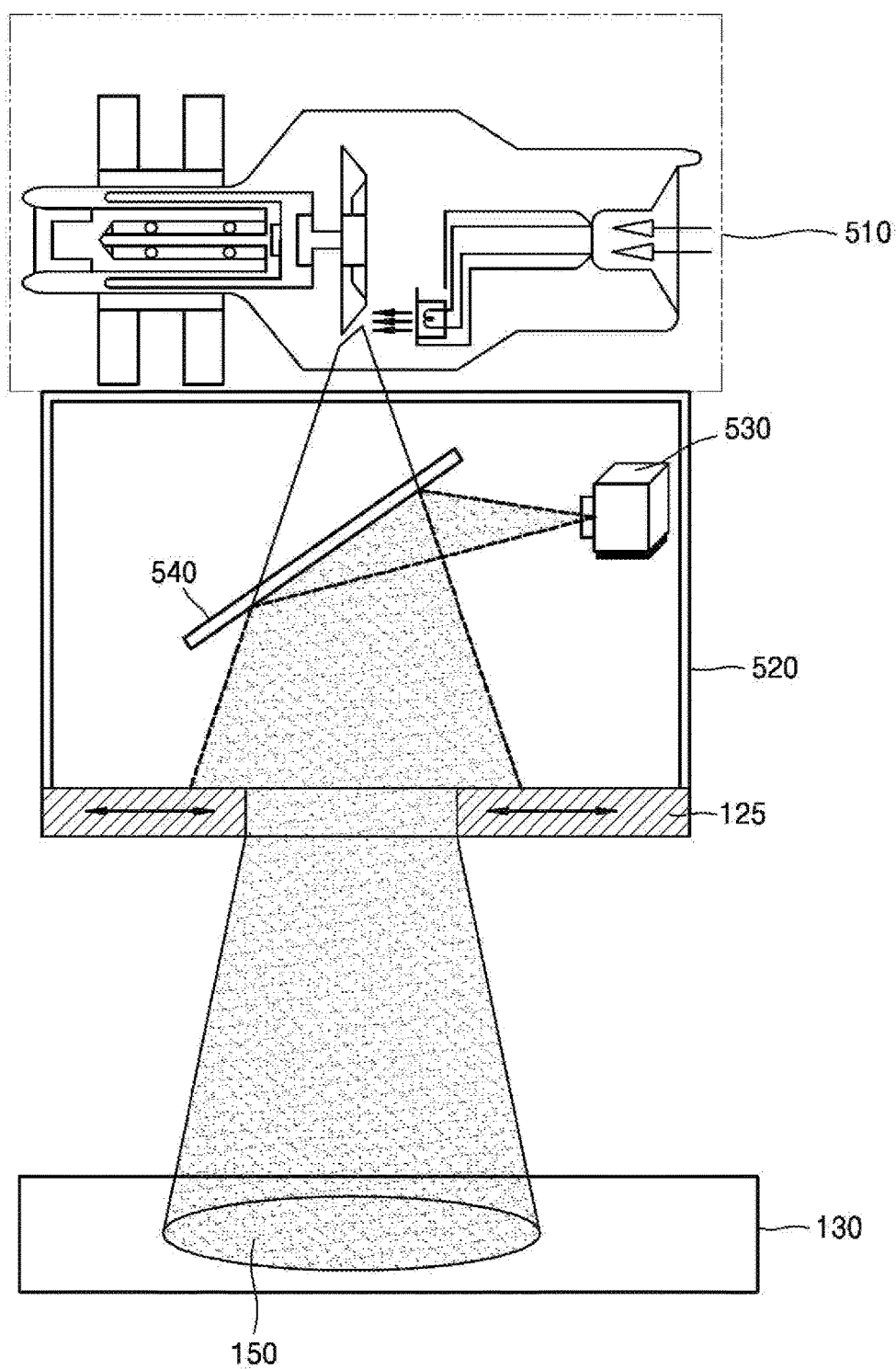
FIG. 11 is a diagram showing a light irradiation field in an X-ray photographing apparatus according to an exemplary embodiment.

FIG. 11 is a diagram showing a light irradiation field in an X-ray photographing apparatus according to an exemplary embodiment.

As shown in FIG. 11, the X-ray photographing apparatus 500*a* may include the projector 530 for generating and projecting a visible ray image that may be recognized by a user and the reflection mirror 540 for reflecting and irradiating the visible ray image projected by the projector 530 to a target object to be photographed.

Therefore, a user may visually recognize an area of irradiation of an X-ray as a visible ray image generated and irradiated by the projector 530 and is reflected by the reflection mirror 540 that is arranged tilted behind a collimator.

For example, as shown in FIG. 11, an area at which a visible ray image irradiated via the irradiation field area adjusting unit 125 intersects with the light receiving surface of the detector 130 may be referred to as the light irradiation field 150, where the light irradiation field 150 may be changed based on a location of the visible ray image projected by the projector 530 and/or a size of the visible ray image projected by the projector 530.

Furthermore, a visible ray image corresponding to a light irradiation field is a 2-dimensional image that is generated based on image signals received from an external source and may include pictures or texts. Therefore, an X-ray photographing apparatus according to an exemplary embodiment may provide information regarding an X-ray photographing operation or information regarding a target object via a visible ray image corresponding to a light irradiation field to a user for visual recognition.

Figure 12:
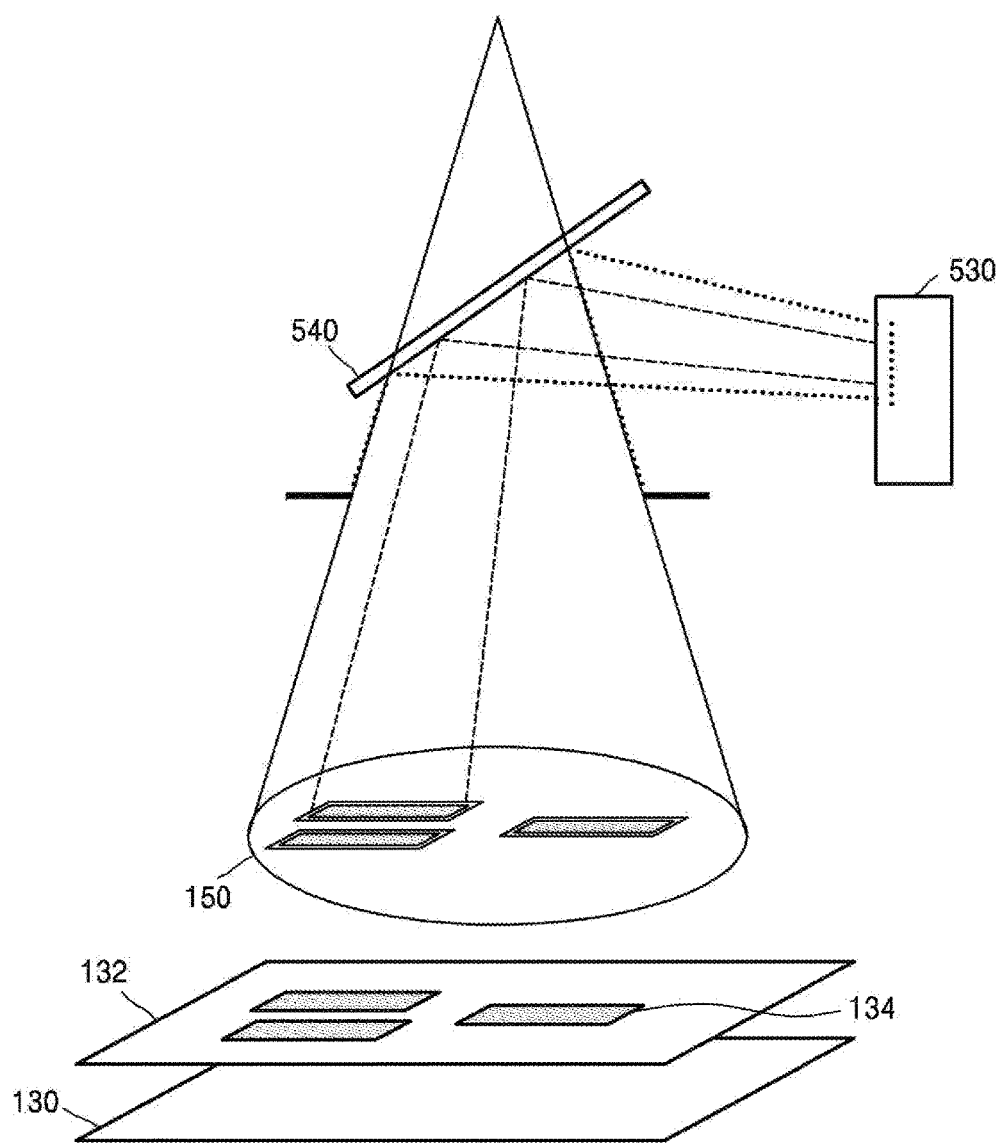
FIGS. 12, 13, and 14 are diagrams showing various examples of visible ray images projected in a light irradiation field according to an exemplary embodiment.
Figure 13:
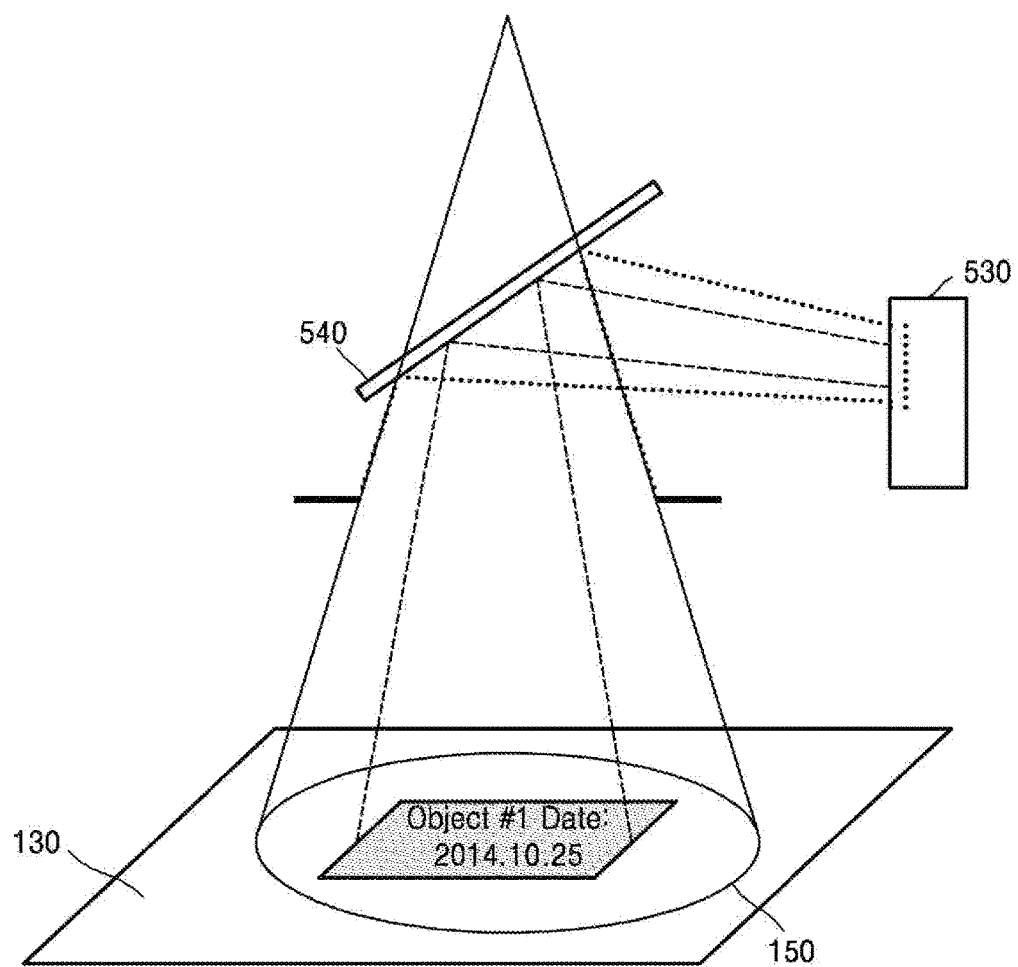
Figure 14:
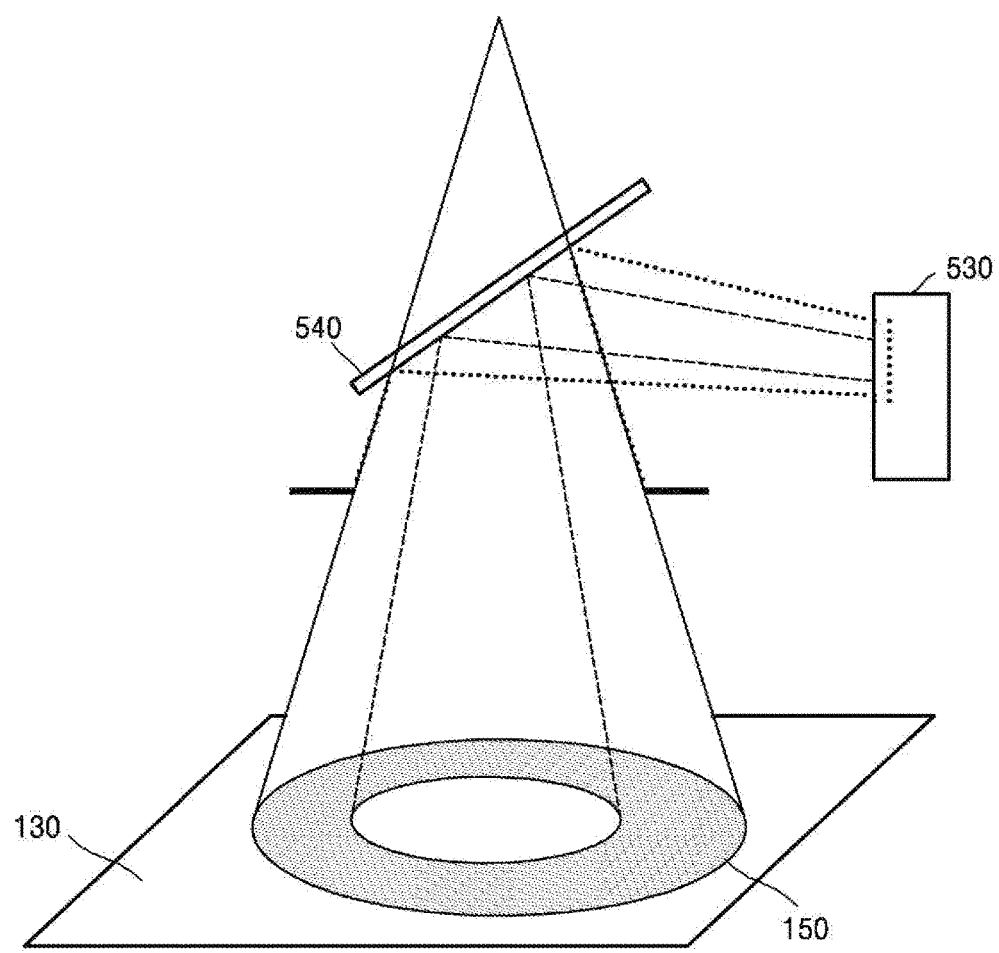

FIGS. 12 through 14 are diagrams showing various examples of visible ray images projected in a light irradiation field according to an exemplary embodiment.

As shown in FIGS. 12 through 14, a 2-dimensional image 134 including shapes of characters or pictures may be displayed in an area corresponding to a light irradiation field as a visible ray image.

Furthermore, a visible ray image projected by the projector 530 may be projected onto a light receiving surface of a detector or a target object located between the detector and a collimator.

For example, as shown in FIG. 12, an AEC (automatic exposure control) apparatus 132, which is an over-irradiation preventing unit, may be arranged between the target object and the detector 130.

For example, a relative location of the AEC apparatus 132 with respect to a target object is an important factor for the AEC apparatus 132. In an X-ray photographing operation, since the AEC apparatus 132 is blocked by a target object, it is difficult to perform the X-ray photographing operation.

Meanwhile, the X-ray photographing apparatus 500*a* according to an exemplary embodiment may perform an X-ray photographing operation more precisely by projecting a visible ray image indicating location of an AEC sensor on a front surface of a target object by using the projector 530 and the reflection mirror 540.

As shown in FIG. 13, a visible ray image corresponding to a light irradiation field 150 includes not only information regarding an area of X-ray irradiation, but also information regarding a photographing operation of the X-ray photographing apparatus or information regarding the target object to be photographed by the X-ray photographing apparatus, where the visible ray image corresponding to a light irradiation field 150 may be displayed on a light receiving surface of the detector 130.

For example, information needed for a photographing operation, such as an X-ray photographing operation progress status indicating that it is before, during, or after the X-ray photographing operation, information regarding a target object, a photographing protocol, and time, may be indicated in an X-ray photographing area in texts or pictures, where, for example, status of an equipment may be indicated with colors.

Furthermore, as shown in FIG. 14, visible rays may or may not be selectively projected to a detector or a target object located between the detector and a collimator. Furthermore, color of an irradiated visible ray may be changed entirely or partially.

For example, aside from projection of information, visible rays may not be irradiated to any area where they are not supposed to be irradiated.

For example, in a technique for photographing a face of a person, a light generated by a collimator during adjustment of an irradiation field may blind a person's eyes, and thus it is difficult to maintain an appropriate photographing position.

The phenomenon occurs because a collimator may not be able to selectively limit an amount of light irradiated to a portion of a light irradiation field. However, as shown in FIG. 14, the X-ray photographing apparatus 500*a* according to an exemplary embodiment may selectively limit the amount of light irradiated to the portion of the light irradiation field, and thus the X-ray photographing apparatus 500*a* may be controlled to prevent light from entering into the eyes of a patient.

Figure 15:
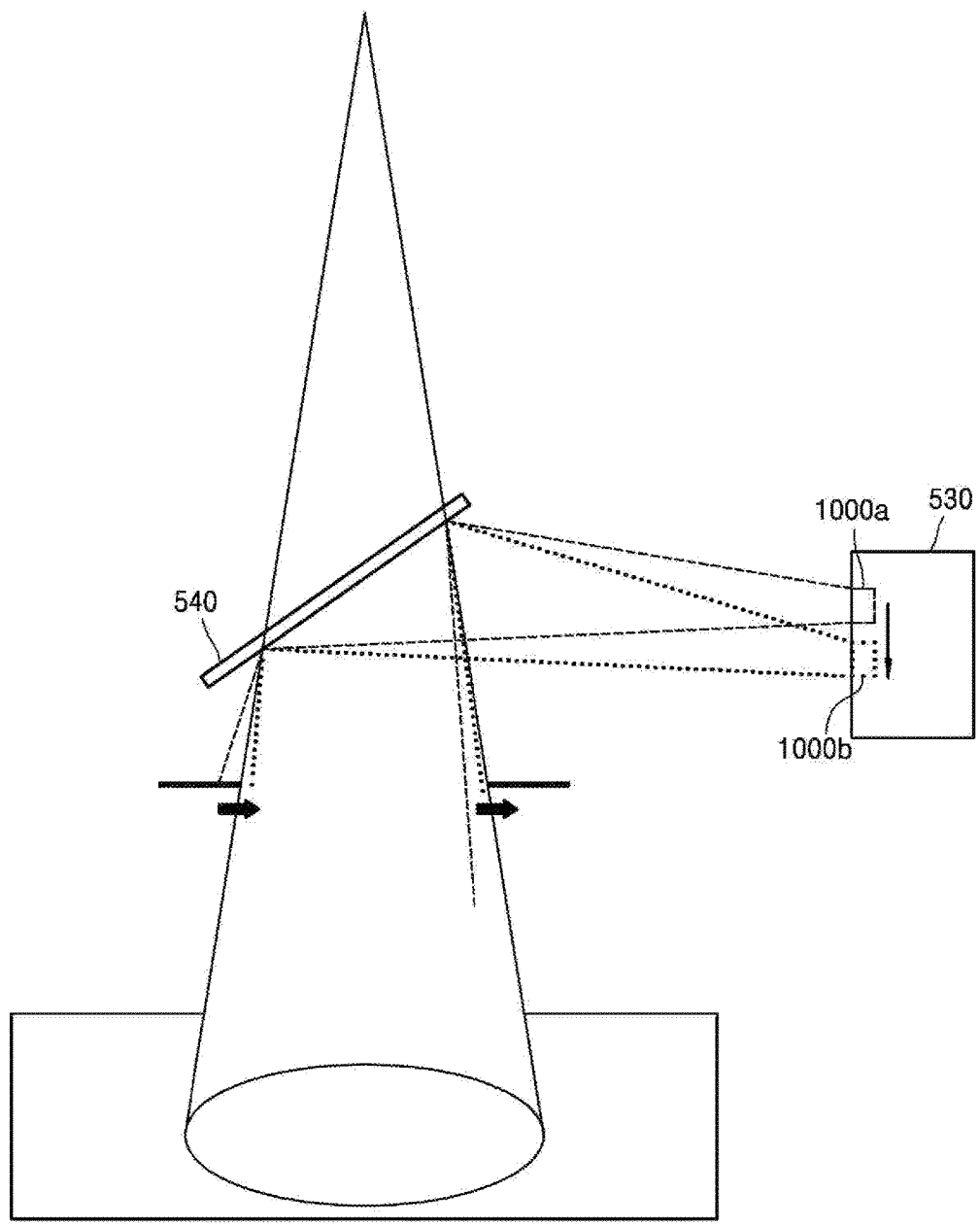
FIGS. 15, 16 and 17 are diagrams showing a mechanism for matching an X-ray irradiation field to a light irradiation field in an X-ray photographing apparatus according to an exemplary embodiment.
Figure 16:
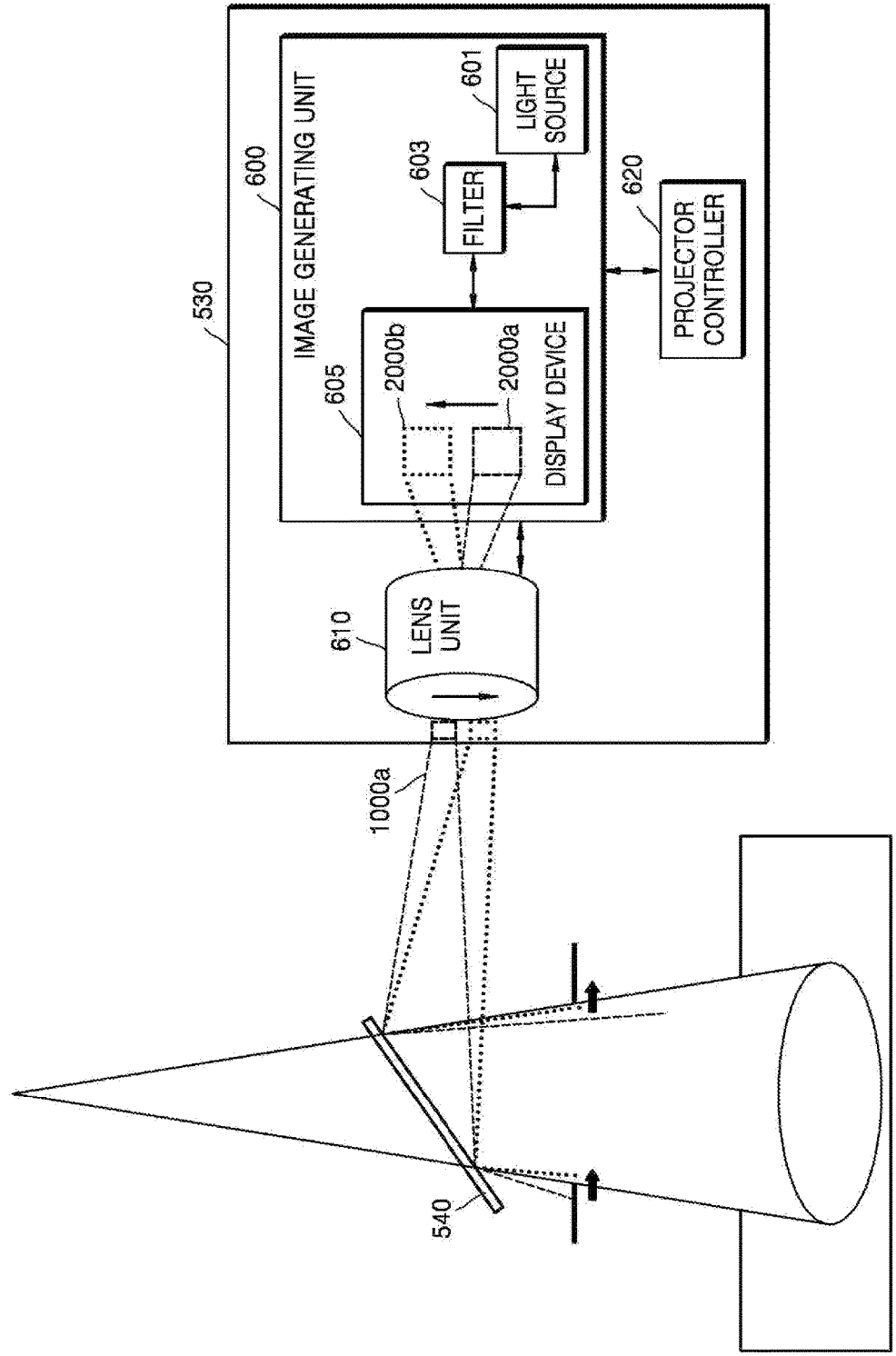
Figure 17:
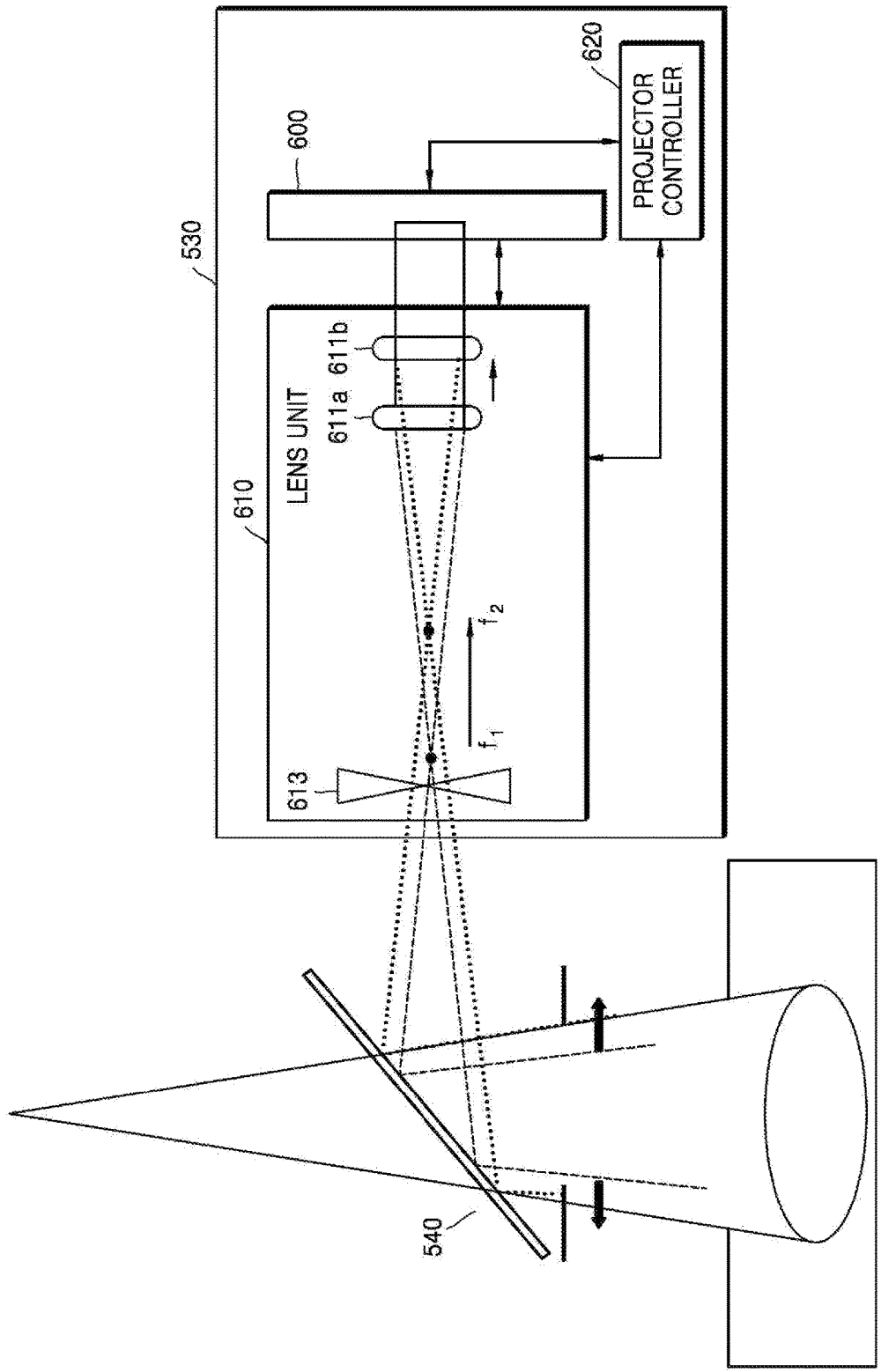

FIGS. 15 through 17 are diagrams showing the mechanism for matching an X-ray irradiation field to a light irradiation field in an X-ray photographing apparatus according to an exemplary embodiment.

A visible ray image corresponding to a light irradiation field according to an exemplary embodiment may be determined based on location and/or size of a visible ray image projected by a projector.

Therefore, as shown in FIG. 15, if a visible ray image is projected by the projector 530 at a location 1000*a*, a path in which a visible ray travels may not match a path in which an X-ray is irradiated by an X-ray source.

In this case, to match a light irradiation field to an X-ray irradiation field, it is necessary to match a path in which a visible ray travels to a path in which an X-ray is irradiated by an X-ray source. As shown in FIG. 15, if the visible ray image projected by the projector is moved to a location 1000*b*, the light irradiation field may be matched to the X-ray irradiation field.

In other words, unlike a collimator in which location of a point light source and/or a reflection mirror is precisely controlled by using a mechanical adjusting unit including 3 or more axes, an X-ray photographing apparatus according to an exemplary embodiment may match a light irradiation field to an X-ray irradiation field by adjusting location of a visible ray image projected by a projector via a main controller of the X-ray photographing apparatus or a projector controller of the projector without a mechanical adjustment.

As described above with reference to FIG. 15, when a location of the visible ray image projected by the projector 530 is changed, a location of a visible ray image generated by the image generating unit 600 is changed as shown in FIG. 16.

For example, a visible ray image may be generated by the image generating unit 600 by converting image signals to a projection image via the display device 605 by using a light provided by a light source 601.

Furthermore, image signals may be converted to a projection image by using only pixels included in an active area of the display device 605. In this case, the active area may be determined by the projector controller 620.

In other words, a location of a visible ray image generated by the image generating unit 600 varies according to a location of active area in the display device 605, and thus a location of a visible ray image projected by the projector 530 varies as well.

As shown in FIG. 16, when a projection image converted by the display device 605 by using a first active area 2000*a* is transmitted through the lens unit 610, a visible ray image is projected to the location 1000*a* by the projector 530. In this case, if the projector 530 projects visible rays to the location 1000*a*, a path in which a visible ray travels does not match a path in which an X-ray is irradiated by an X-ray source.

Here, the main controller of the X-ray photographing apparatus according to an exemplary embodiment may control the projector controller 620 to change location to which the visible ray image is projected by the projector 530 from the location 1000*a* to the location 1000*b*.

As shown in FIG. 16, when a projection image converted by the display device 605 by using a second active area 2000*b* is transmitted through the lens unit 610, a visible ray image is projected to the location 1000*b* by the projector 530. In this case, if the projector 530 projects visible rays to the location 1000*b*, a path in which a visible ray travels matches a path in which an X-ray is irradiated by an X-ray source.

In other words, as a location of an active area of the display device 605 is adjusted by the projector controller 620, a path in which a visible ray travels matches a path in which an X-ray is irradiated by an X-ray source. Therefore, location of a visible ray image corresponding to a light irradiation field may match location of an X-ray irradiation field.

Therefore, an X-ray photographing apparatus according to an exemplary embodiment may match a light irradiation field to an X-ray irradiation field by changing location of a visible ray image projected by the projector 530 without a mechanical adjustment.

On the contrary, the projector controller 620 may control the lens unit 610 included in the projector 530, thereby controlling a size and/or focus of a visible ray image projected by the projector 530.

For example, a visible ray image generated by the image generating unit 600 may be focused at the lens unit 610. In this case, the lens unit 610 may include a plurality of lenses, and the projector controller 620 may adjust the locations of one or more of the plurality of lenses, thereby controlling a size and/or focus of the visible ray image projected by the projector 530.

For example, the lens unit 610 may consist of a zoom lens, which is a mechanical combination of a plurality of lenses and is capable of changing a focal length, where, as the location of one or more of the lenses included in the zoom lens are adjusted, size and/or focus location of the visible ray image projected by the projector 530 may be controlled.

For example, as shown in FIG. 17, when a visible ray image generated by the image generating unit 600 is transmitted through the lens unit 610 consisting of a plurality of lenses 611a and 613 with a focal length f1, a size of a visible ray image projected by the projector 530 becomes smaller than that of an X-ray irradiation field, and thus a light irradiation field 150 may not match the X-ray irradiation field.

Here, the main controller of an X-ray photographing apparatus according to an exemplary embodiment may control the projector controller 620, thereby controlling a focal length of the lens unit 610.

For example, the projector controller 620 may adjust the locations of one or more of a plurality of lenses included in the lens unit 610, thereby changing a focal length of the lens unit 610 from f1 to f2. In this case, as shown in FIG. 17, when a visible ray image generated by the image generating unit 600 is transmitted through the lens unit 610 consisting of a plurality of lenses 611b and 613 with a focal length f2, a size of a visible ray image projected by the projector 530 becomes identical to that of an X-ray irradiation field.

Therefore, an X-ray photographing apparatus according to an exemplary embodiment may match a light irradiation field to an X-ray irradiation field by changing size of a visible ray image projected by the projector 530 without a mechanical adjustment.

Figure 18:
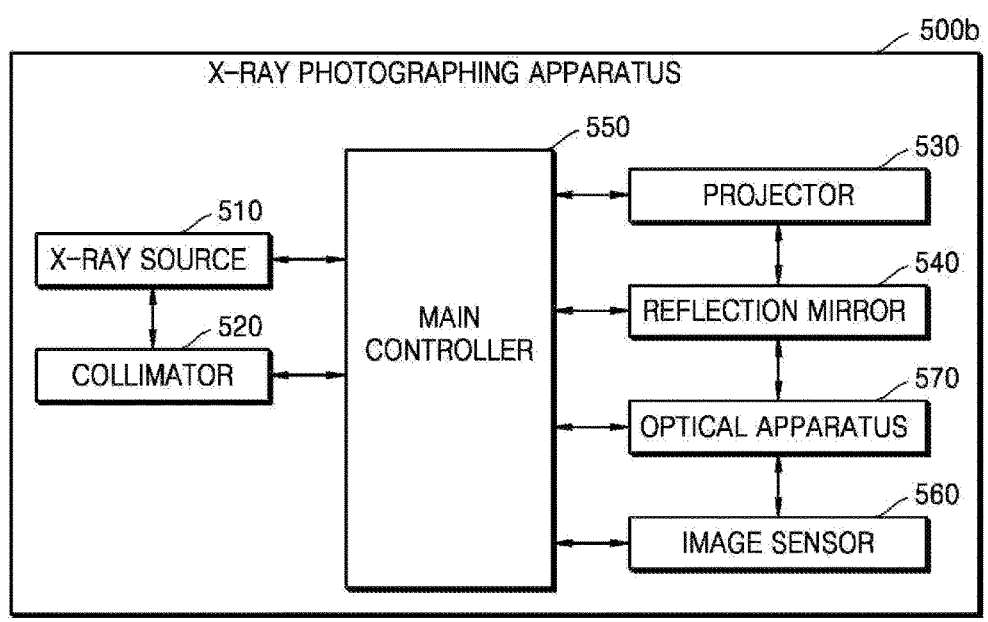
FIG. 18 is a block diagram of an X-ray photographing apparatus according to an exemplary embodiment, where the X-ray photographing apparatus further includes an image sensor for photographing a visible ray image corresponding to an X-ray irradiation field.

FIG. 18 is a block diagram of an X-ray photographing apparatus 500b according to an exemplary embodiment, where the X-ray photographing apparatus 500b further includes an image sensor for photographing a visible ray image corresponding to an X-ray irradiation field.

The X-ray photographing apparatus 500b according to an exemplary embodiment may further include optical apparatus 570 and an image sensor 560.

The optical apparatus 570 according to an exemplary embodiment may be located close to a reflection mirror, thus being capable of focusing a photographing light corresponding to an X-ray photographing area.

For example, the optical apparatus 570 may be a revolving mirror 550a or a beam splitter 550b.

The image sensor 560 according to an exemplary embodiment may receive a photographing light focused by the optical apparatus 570.

For example, an image sensor may be a charge-coupled device (CCD) or a complementary metal-oxide semiconductor (CMOS) for converting optical signals reflected by an optical apparatus to electric signals.

Detailed descriptions thereof will be given below with reference to FIGS. 20A through 20D.

Furthermore, based on a positional relationship between an optical apparatus and an image sensor, the image sensor may receive a photographing light reflected by the optical apparatus or a photographing light transmitted through the optical apparatus. Detailed descriptions thereof will be given below with reference to FIGS. 21A and 21B.

Figure 19:
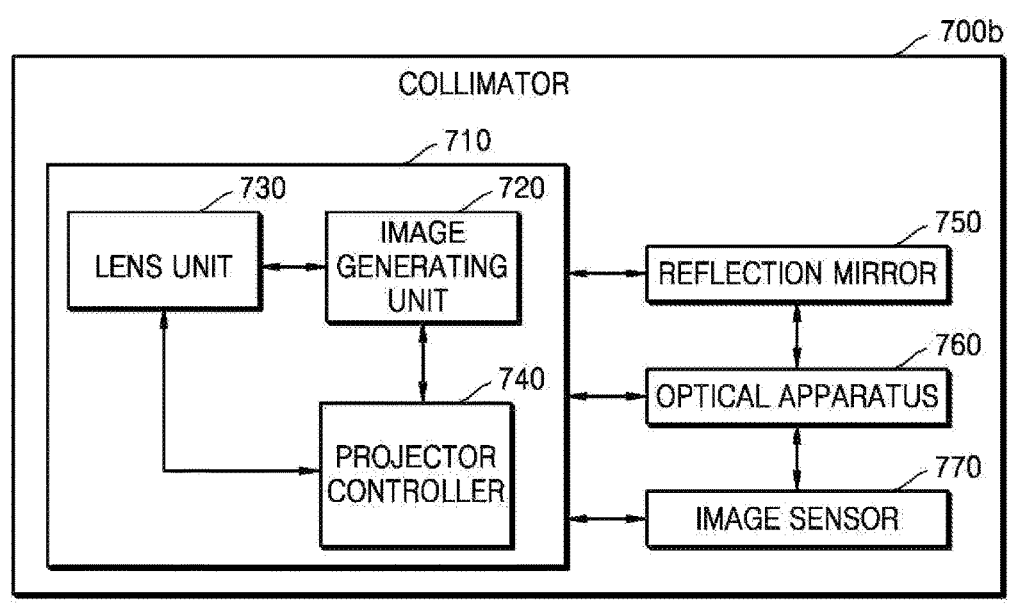
FIG. 19 is a block diagram of a collimator including an image sensor, according to an exemplary embodiment.

FIG. 19 is a block diagram of a collimator 700b including an image sensor, according to an exemplary embodiment.

As shown in FIG. 19, the collimator 700b according to an exemplary embodiment may include an optical apparatus 760 and an image sensor 770.

If the collimator 700b of FIG. 19 is included in the X-ray photographing apparatus 500b of FIG. 18, the optical apparatus 760 and the image sensor 770 of FIG. 19 may be identical to the optical apparatus 570 and the image sensor 560 of FIG. 18. Therefore, descriptions thereof given above with reference to FIG. 18 will be omitted.

FIGS. 20A through 20D are diagrams showing various examples in which an X-ray photographing apparatus according to an exemplary embodiment captures visible ray images corresponding to an X-ray photographing area by using the revolving mirror 550a and the image sensor 560.

According to an exemplary embodiment, an X-ray photographing area of a light receiving surface may be photographed via an image sensor. Therefore, a user may precisely recognize an X-ray photographing area corresponding to an X-ray irradiation field or a light irradiation field by photographing the same in real time.

Figure 20A:
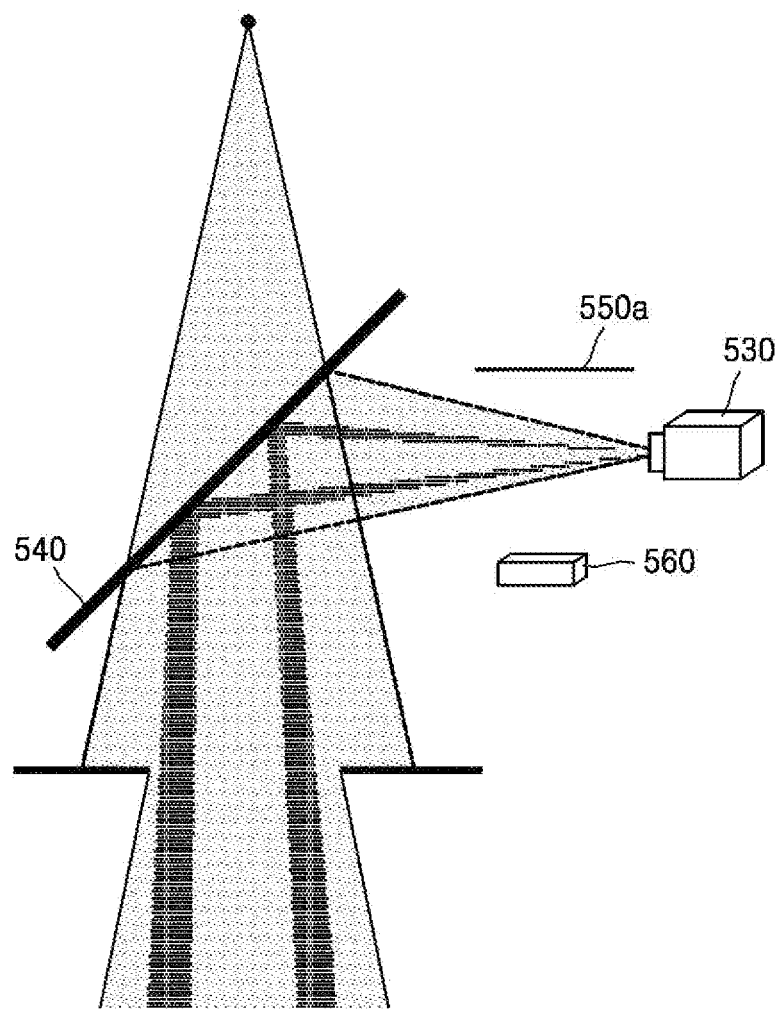
FIGS. 20A, 20B, 20C, and 20D are diagrams showing various examples in which an X-ray photographing apparatus according to an exemplary embodiment captures visible ray images corresponding to an X-ray photographing area by using a revolving mirror and an image sensor.
Figure 20B:
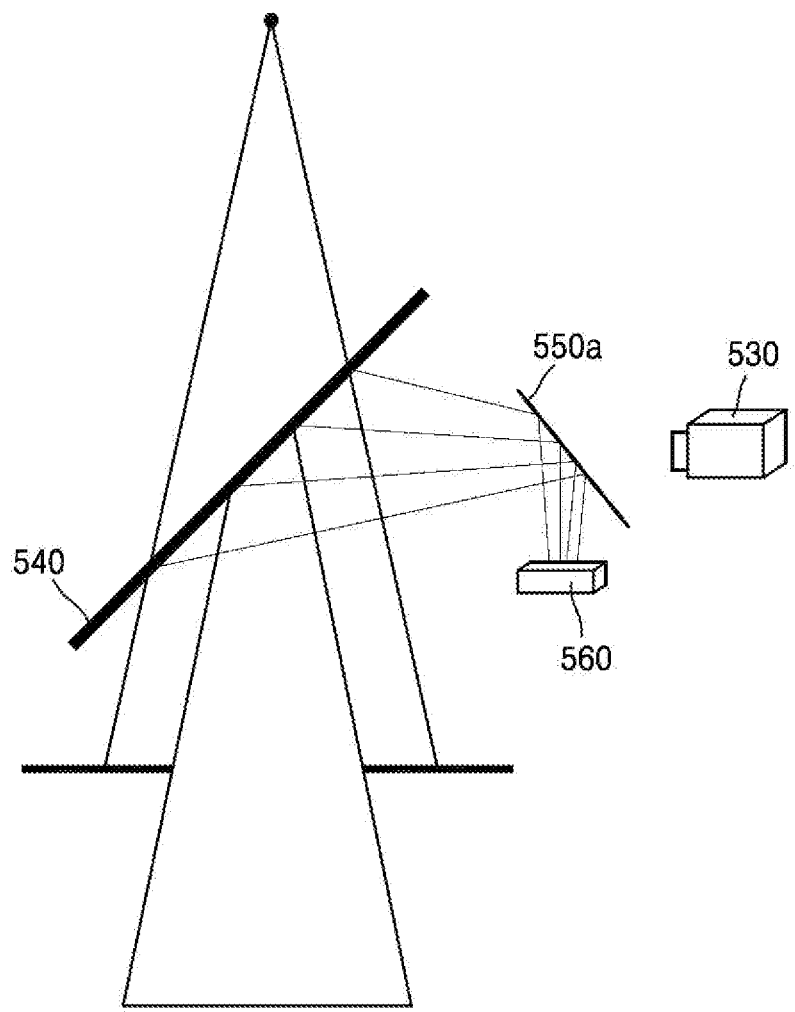

As shown in FIGS. 20A and 20B, the revolving mirror 550a (optical apparatus) may be located and revolve between the reflection mirror 540 and the projector 530.

For example, as shown in FIG. 20A, if the revolving mirror 550a is not located on a path in which a visible ray projected by the projector 530 travels, a visible ray image projected by the projector 530 may be reflected by the reflection mirror 540 and projected to a light receiving surface.

For example, a visible ray image projected to a light receiving surface may include not only information regarding an area of X-ray irradiation, but also information regarding a photographing operation of an X-ray photographing apparatus or information regarding a target object to be photographed by the X-ray photographing apparatus.

Furthermore, as shown in FIG. 20B, if the revolving mirror 550a is located on the path in which a visible ray projected by the projector 530 travels and is tilted, a photographing light corresponding to the X-ray photographing area of the light receiving surface may be reflected by the reflection mirror 540 and the revolving mirror 550a and received by the image sensor 560, and the X-ray photographing area of the light receiving surface may be photographed based on the photographing light received by the image sensor 560.

However, in this case, a visible ray irradiated by the projector 530 is blocked by the revolving mirror 550a and is unable to travel to the reflection mirror 540.

Therefore, as shown in FIGS. 20A and 20B, based on orientation of the revolving mirror 550a located between the reflection mirror 540 and the projector 530, a visible ray image projected by the projector 530 may be projected to the light receiving surface or the X-ray photographing area of the light receiving surface may be photographed via the image sensor. However, projection of a visible ray image and photographing of an X-ray photographing area may not occur simultaneously.

Figure 20C:
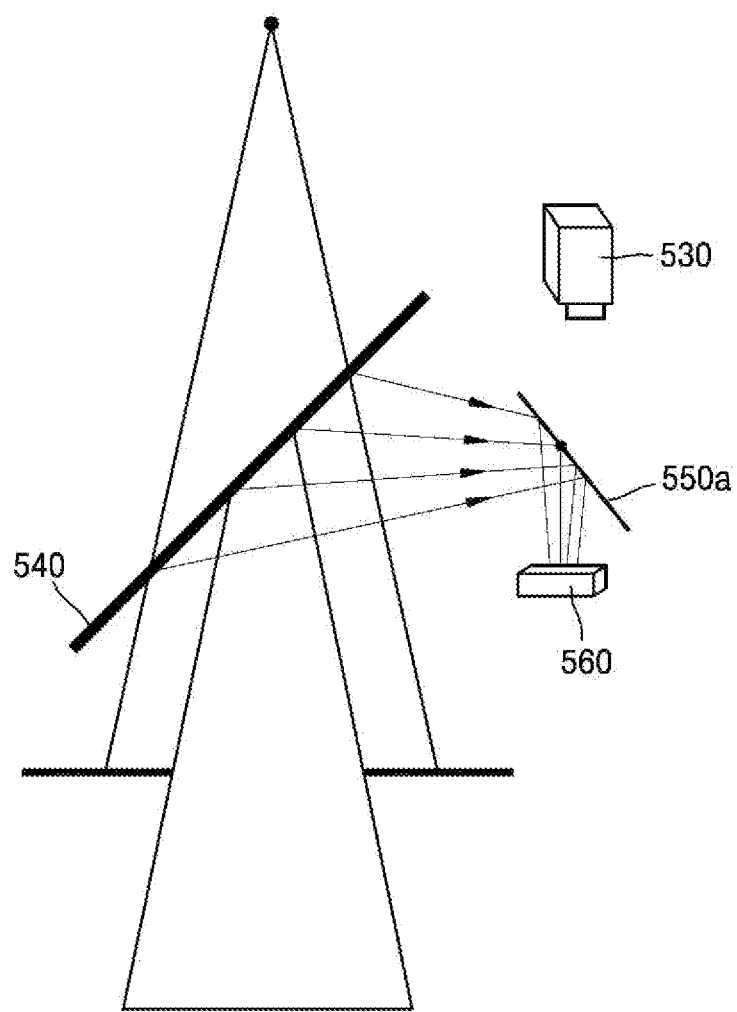
Figure 20D:
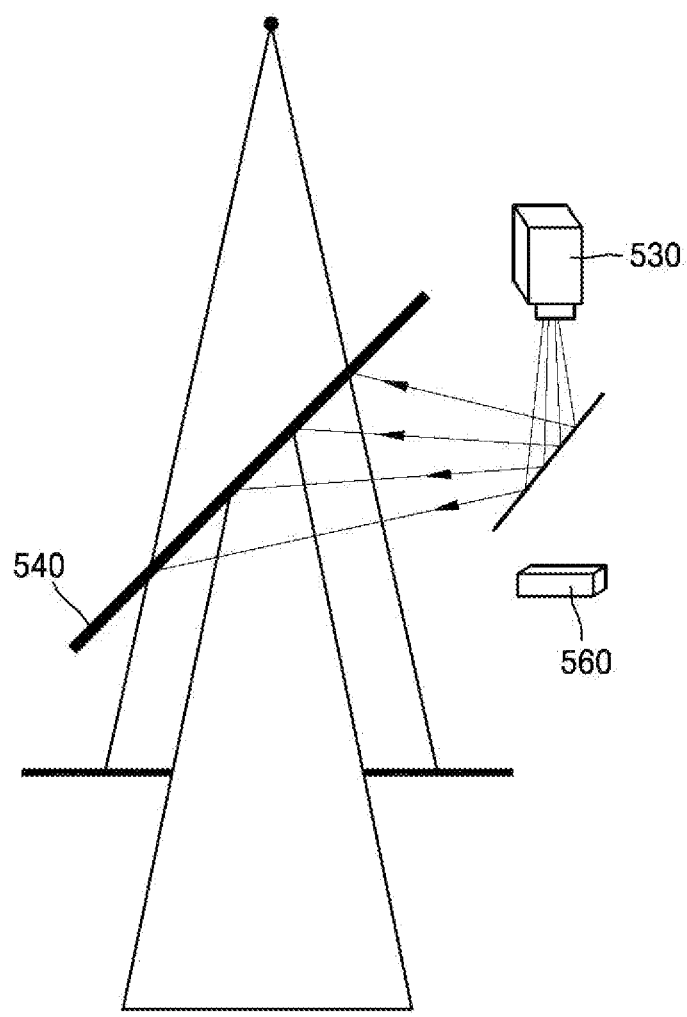

As shown in FIGS. 20C and 20D, the revolving mirror 550a (optical apparatus) may be located between the projector 530 and the image sensor 560 and revolve.

For example, if the revolving mirror 550a is located as shown in FIG. 20C, a photographing light corresponding to the X-ray photographing area of the light receiving surface may be reflected by the reflection mirror 540 and the revolving mirror 550a and received by the image sensor 560, and thus the X-ray photographing area of the light receiving surface may be photographed.

However, in this case, a visible ray irradiated by the projector 530 is blocked by the revolving mirror 550a and is unable to travel to the reflection mirror 540.

Furthermore, if the revolving mirror 550a is located as shown in FIG. 20D, a visible ray image projected by the projector 530 may be reflected by the reflection mirror 540 and projected to the light receiving surface.

For example, a visible ray image projected to a light receiving surface may include not only information regarding an area of X-ray irradiation, but also information regarding a photographing operation of an X-ray photographing apparatus or information regarding a target object to be photographed by the X-ray photographing apparatus.

However, in this case, a visible ray irradiated by the projector 530 may not be received by the image sensor 560 due to the revolving mirror 550a.

Therefore, as shown in FIGS. 20C and 20D, based on orientation of the revolving mirror 550a located between the reflection mirror 540 and the image sensor 560, a visible ray image projected by the projector 530 may be projected to the light receiving surface or the X-ray photographing area of the light receiving surface may be photographed via the image sensor. However, projection of a visible ray image and photographing of an X-ray photographing area may not occur simultaneously.

Figure 21A:
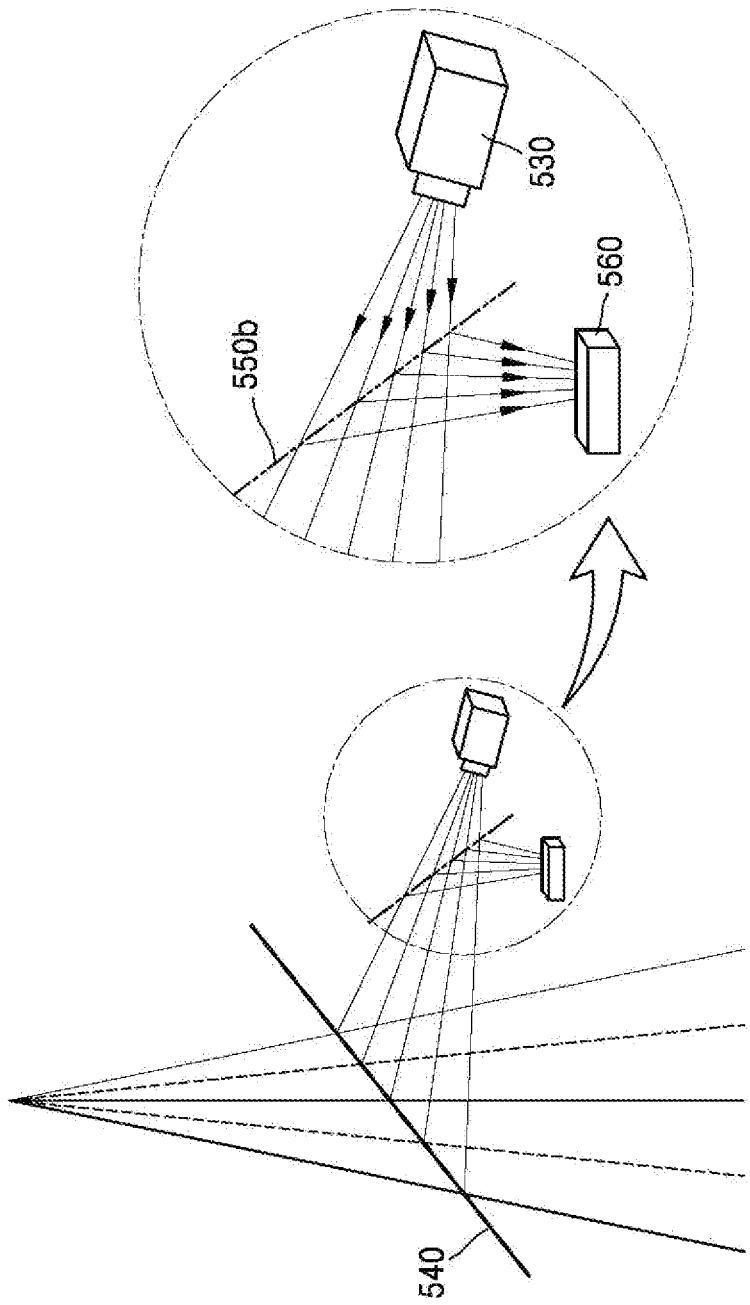
FIGS. 21A and 21B are diagrams showing various examples in which an X-ray photographing apparatus according to an exemplary embodiment captures visible ray images corresponding to an X-ray photographing area by using a beam splitter and an image sensor.
Figure 21B:
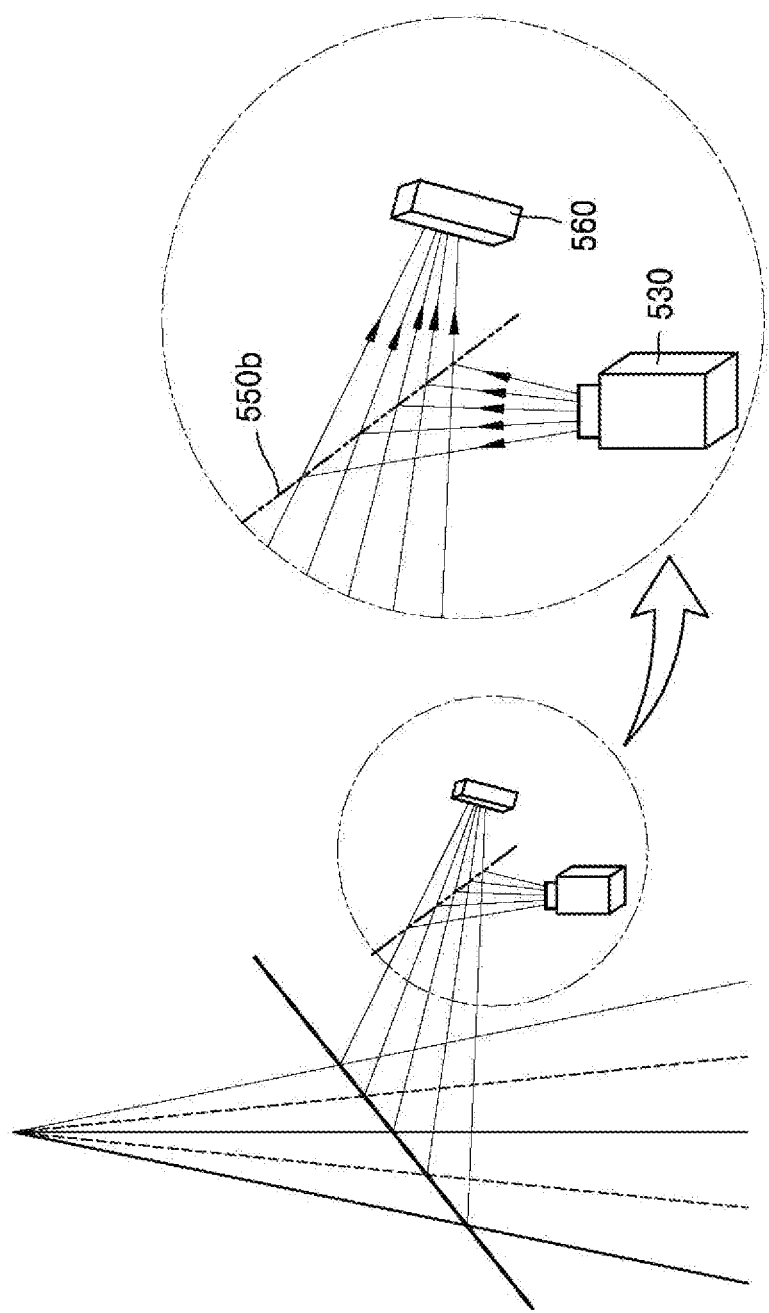

FIGS. 21A and 21B are diagrams showing various examples in which an X-ray photographing apparatus according to an exemplary embodiment captures visible ray images corresponding to an X-ray photographing area by using the beam splitter 550b and the image sensor 560.

The beam splitter 550b is an optical apparatus formed of a special material and is capable of splitting an incident light according to a desired condition. For example, the beam splitter 550b may split an incident light according to wavelengths and may also reduce the intensity of an incident light.

The beam splitter 550b (optical apparatus) according to an exemplary embodiment may reflect a part of a visible ray and transmit the other part of the visible ray therethrough.

For example, if the beam splitter 550b is located between the reflection mirror 540 and the projector 530 as shown in FIG. 21A, a part of a visible ray irradiated by the projector 530 may be transmitted through the beam splitter 550b.

In this case, a part of the visible ray transmitted through the beam splitter 550b may be projected to a light receiving surface by the reflection mirror 540. Here, a visible ray image projected to the light receiving surface is the visible ray transmitted through the beam splitter 550b, and thus intensity of the visible ray image projected to the light receiving surface may be weaker than that of a visible ray image directly projected by the projector 530.

Furthermore, if the beam splitter 550b is located between the reflection mirror 540 and the projector 530 as shown in FIG. 21A, a photographing light corresponding to an X-ray photographing area of the light receiving surface may be reflected by the reflection mirror 540 and the beam splitter 550b and received by the image sensor 560.

In this case, the X-ray photographing area of the light receiving surface may be photographed based on the visible ray received by the image sensor 560. Here, a visible ray of the X-ray photographing area received by the image sensor 560 is a visible ray reflected from a photographing light by the beam splitter 550b, and thus intensity of the X-ray photographing area received by the image sensor 560 may be weaker than that of the photographing light of the X-ray photographing area.

For example, if the beam splitter 550b is located between the reflection mirror 540 and the image sensor 560 as shown in FIG. 21B, a part of a visible ray irradiated by the projector 530 may be reflected by the beam splitter 550b.

In this case, the part of the visible ray reflected by the beam splitter 550b may be projected to the light receiving surface. Here, a visible ray image projected to the light receiving surface is a visible ray reflected by the beam splitter 550b from a visible ray irradiated by the projector 530, and thus intensity of the visible ray image projected to the light receiving surface may be weaker than that of a visible ray image directly projected by the projector 530.

Furthermore, if the beam splitter 550b is located between the reflection mirror 540 and the image sensor 560 as shown in FIG. 21B, a photographing light corresponding to the X-ray photographing area of the light receiving surface may be reflected by the reflection mirror 540, transmitted through the beam splitter 550b, and received by the image sensor 560.

In this case, the X-ray photographing area of the light receiving surface may be photographed based on the visible ray received by the image sensor 560. Here, a visible ray of the X-ray photographing area received by the image sensor 560 is a visible ray transmitted through the beam splitter 550b from a photographing light, and thus intensity of the X-ray photographing area received by the image sensor 560 may be weaker than that of the photographing light of the X-ray photographing area.

Figure 22:
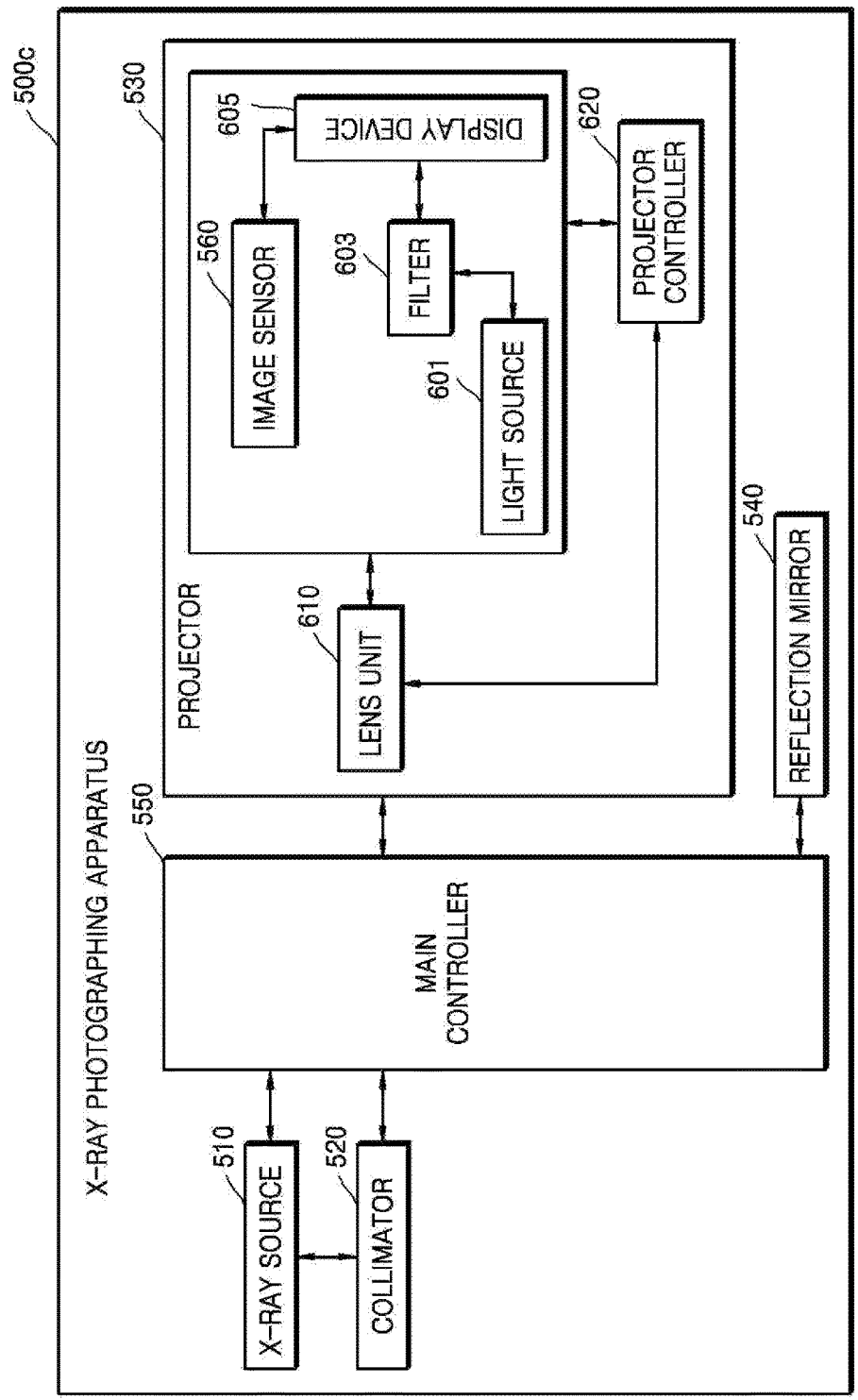
FIG. 22 is a block diagram of an X-ray photographing apparatus according to an exemplary embodiment, further including an image sensor for photographing a visible ray image corresponding to an X-ray photographing area.

FIG. 22 is a block diagram of an X-ray photographing apparatus 500c according to an exemplary embodiment, further including the image sensor 560 for photographing a visible ray image corresponding to an X-ray photographing area.

As shown in FIG. 22, the X-ray photographing apparatus 500c according to an exemplary embodiment may further include the projector 530 and the image sensor 560.

The image sensor 560 according to an exemplary embodiment may receive a light reflected by the display device 605.

For example, if the display device 605 included in the image generating unit 600 of the projector 530 is a DMD, the display device 605 according to an exemplary embodiment may include a plurality of micro-mirrors each of which may be independently operated within a predetermined range of angles.

In this case, the image sensor 560 may receive a light focused by the lens unit 610 and reflected by the plurality of micro-mirrors, and thus an X-ray photographing area corresponding to a photographing light focused by the lens unit 610 may be photographed.

Detailed descriptions thereof will be given below with reference to FIG. 26.

Figure 23:
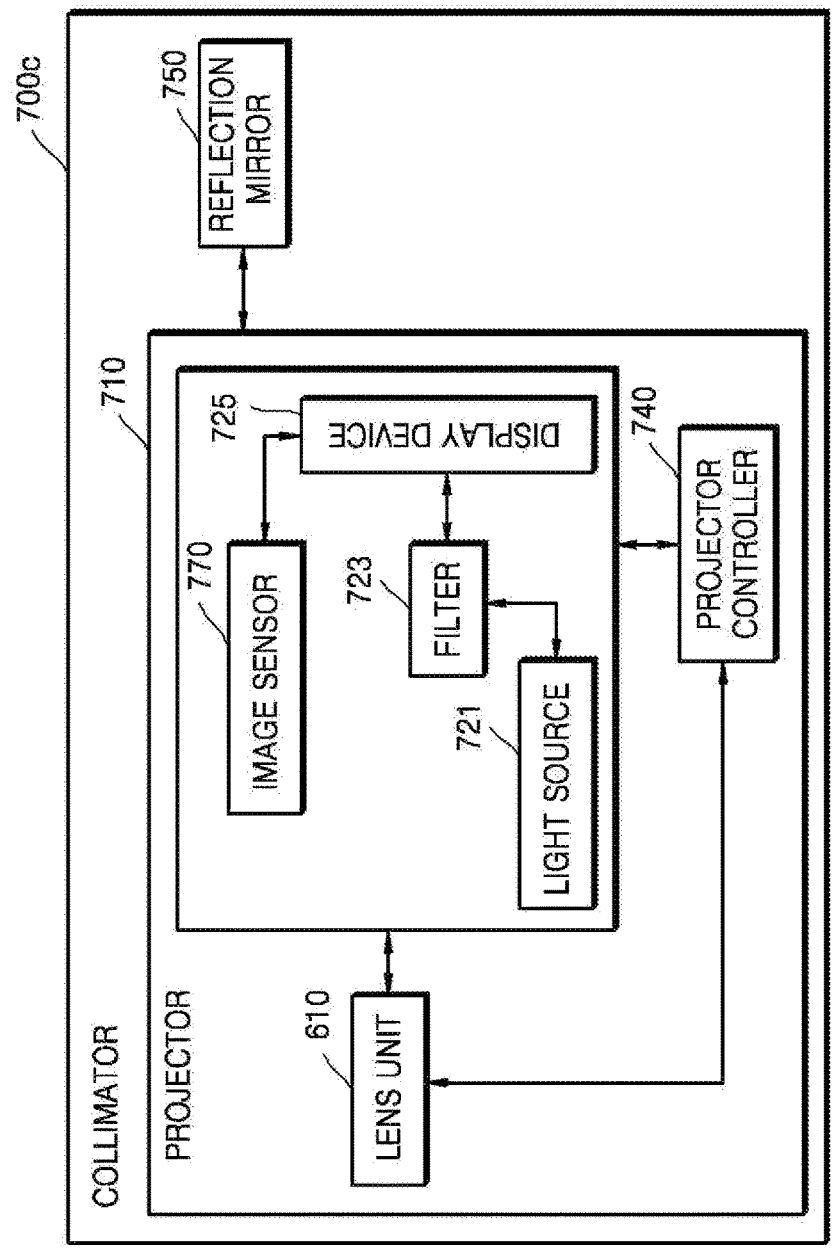
FIG. 23 is a block diagram of a collimator including an image sensor, according to an exemplary embodiment.

FIG. 23 is a block diagram of a collimator 700c including an image sensor, according to an exemplary embodiment.

If the collimator 700c of FIG. 23 is included in the X-ray photographing apparatus 500c of FIG. 22, an image sensor 770 of FIG. 23 may be identical to the image sensor 560 of FIG. 22, and light source 721, filter 723, and display device 725 of FIG. 23 may be identical to the light source 601, filter 603, and display device 605 of FIG. 22, respectively. Therefore, descriptions thereof given above with reference to FIG. 22 will be omitted.

Figure 24:
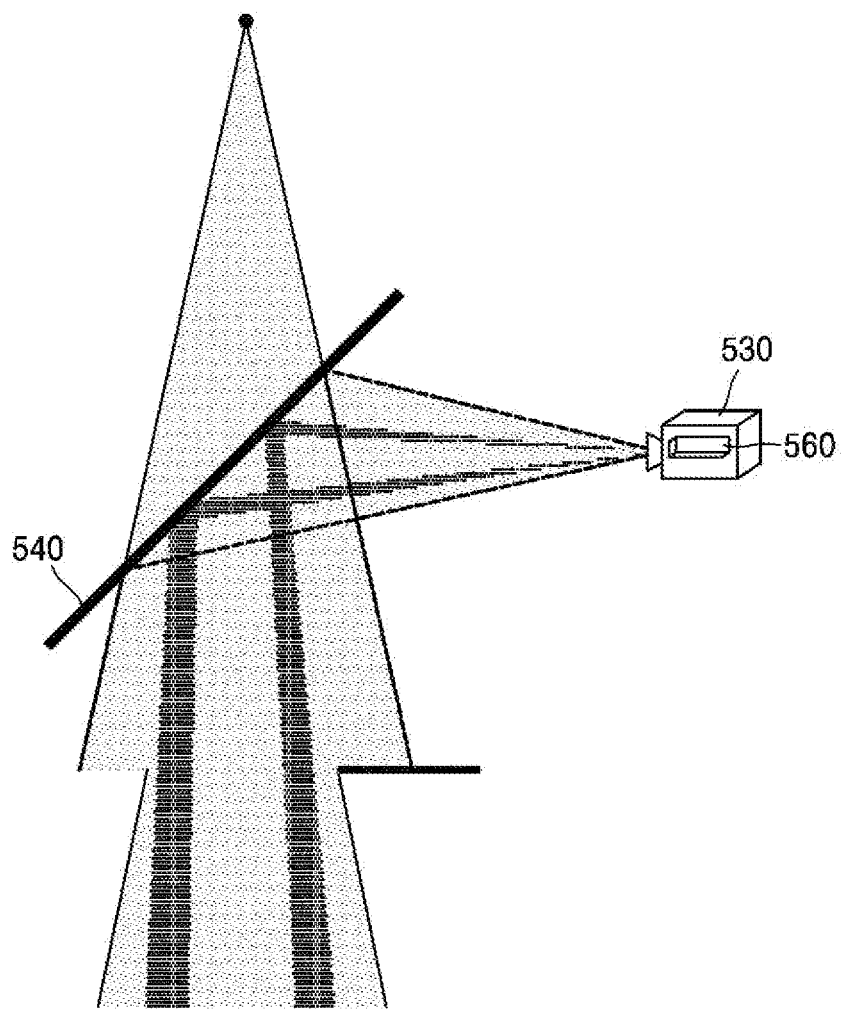
FIG. 24 is a diagram showing an example in which an X-ray photographing apparatus according to an exemplary embodiment captures a visible ray image corresponding to an X-ray photographing area by using a reflection mirror and an image sensor.

FIG. 24 is a diagram showing an example in which an X-ray photographing apparatus according to an exemplary embodiment captures a visible ray image corresponding to an X-ray photographing area by using a reflection mirror and an image sensor.

The X-ray photographing apparatus as shown in FIGS. 20A through 21B may photograph a visible ray image corresponding to an X-ray photographing area by using the reflection mirror 540, the optical apparatuses 500a and 500b and the image sensor 560.

However, an X-ray photographing apparatus according to an exemplary embodiment as shown in FIG. 24 may photograph a visible ray image corresponding to an X-ray photographing area only with the reflection mirror 540 and the image sensor 560.

Figure 25:
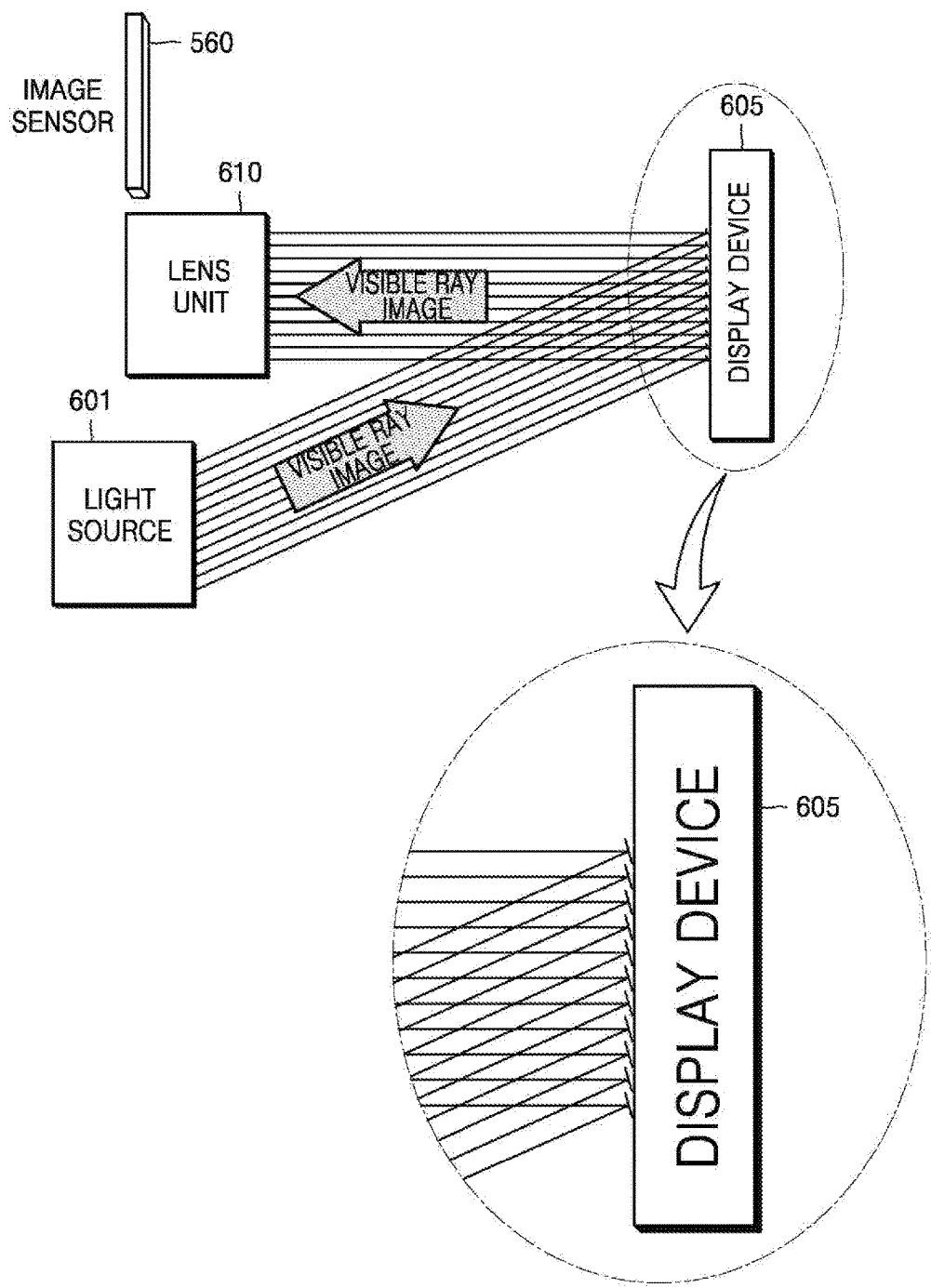
FIGS. 25, 26, and 27 are diagrams showing examples in which an X-ray photographing apparatus according to an exemplary embodiment captures visible ray images corresponding to an X-ray photographing area by using the display device and the image sensor.
Figure 26:
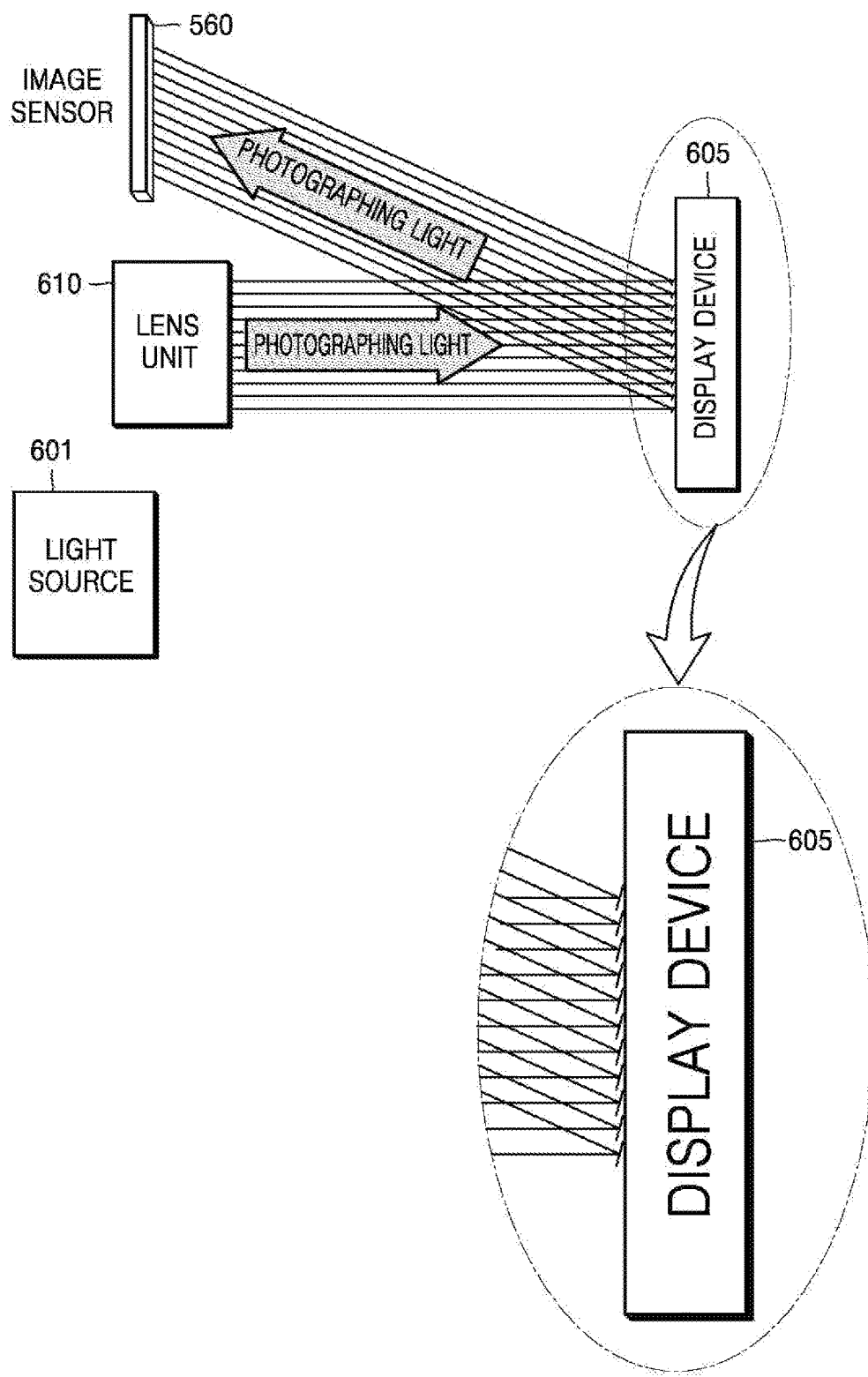
Figure 27:
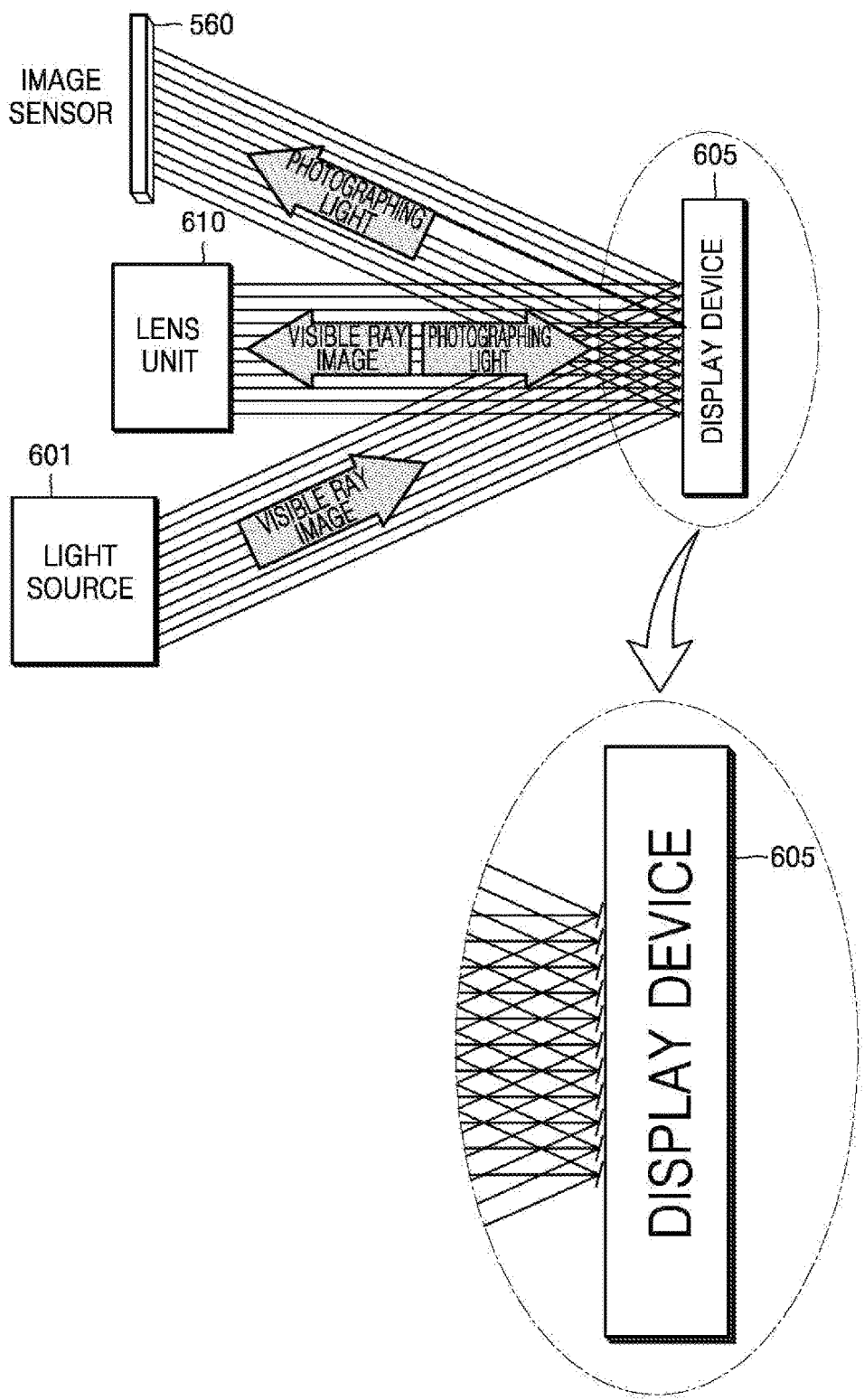

FIGS. 25 through 27 are diagrams showing examples in which an X-ray photographing apparatus according to an exemplary embodiment captures visible ray images corresponding to an X-ray photographing area by using the display device 605 and the image sensor 560.

As shown in FIG. 25, if the display device 605 of the projector 530 is a DMD consisting of a plurality of micro-mirrors with predetermined orientations, the projector 530 may generate a visible ray image by using all of the micro-mirrors included in the display device 605.

As shown in FIG. 26, if the display device 605 of the projector 530 is a DMD consisting of a plurality of micro-mirrors having orientations different from those in FIG. 25, the image sensor 560 may receive a photographing light reflected by all of the micro-mirrors included in the display device 605 and photograph a visible ray image corresponding to an X-ray photographing area.

For example, the lens unit 610 may focus a photographing light corresponding to the X-ray photographing area, and the display device 605 may reflect the photographing light focused by the lens unit 610 by using all of the micro-mirrors.

As shown in FIG. 27, if the display device 605 of the projector 530 is a DMD consisting of a plurality of micro-mirrors having orientations different from those in FIGS. 25 and 26, the projector 530 may generate a visible ray image by using all of the micro-mirrors included in the display device 605. Furthermore, the image sensor 560 may receive a photographing light reflected by all of the micro-mirrors included in the display device 605 and photograph a visible ray image corresponding to an X-ray photographing area Furthermore, although not shown, orientations of the plurality of micro-mirrors included in the display device 605 may be adjusted to be different from one another, where it may be determined for each of the plurality of micro-mirrors whether to reflect a light provided by the light source 601 or to reflect a light focused by the lens unit 610 based on an orientation of the corresponding micro-mirror.

In this case, the plurality of micro-mirrors included in the display device 605 may be used for at least one of projection of a visible ray image and photographing of a visible ray image, based on respective orientations of the plurality of micro-mirrors.

As shown in FIGS. 25 through 27, an X-ray photographing apparatus according to an exemplary embodiment may perform at least one of projection of a visible ray image to the light receiving surface and photographing of a visible ray image corresponding to the X-ray photographing area based on respective orientations of the plurality of micro-mirrors included in the display device 605.

Therefore, it may be instantly or partially switched between projection of a visible ray image and capturing of a visible ray image based on subtle differences between angles of micro-mirrors included in a display device, according to an exemplary embodiment.

The exemplary embodiments of the present inventive concept can be written as computer programs and can be implemented in general-use digital computers that execute the programs using a computer readable recording medium. Examples of the computer readable recording medium include magnetic storage media (e.g., ROM, floppy disks, hard disks, etc.), optical recording media (e.g., CD-ROMs, or DVDs), etc.

While the present inventive concept has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in a descriptive sense only and not for purposes of limitation. Therefore, the scope of the present inventive concept is defined not by the detailed description of the invention but by the appended claims, and all differences within the scope will be construed as being included in the present inventive concept.

What is claimed is:

1. An X-ray imaging apparatus comprising:
   an X-ray source configured to generate and irradiate an X-ray to an X-ray imaging area;
   a collimator configured to control the X-ray imaging area;
   a projector configured to generate and project a visible image using image signals;
   a reflection mirror configured to reflect the visible image projected by the projector to the X-ray imaging area;
   an optical apparatus in optical communication with the reflection mirror and configured to focus an imaging light corresponding to the visible image projected to the X-ray imaging area;
   an image sensor configured to receive the imaging light focused at the optical apparatus; and
   a main controller configured to control the projector to match a light irradiation field corresponding to the visible image projected to the X-ray imaging area to an X-ray irradiation field corresponding to the X-ray irradiated to the X-ray imaging area.

2. The X-ray imaging apparatus of claim 1, wherein the projector comprises:
   an image generator configured to generate the visible image using the image signals;
   a plurality of lenses configured to focus the visible image generated by the image generator; and
   a projector controller configured to control at least one of the image generator and at least one of the plurality of lenses.

3. The X-ray imaging apparatus of claim 2, wherein the image generator comprises:
   a display device configured to convert the image signals to a projection image at an active area; and
   a light source configured to generate a visible image from the projection image,
   wherein the active area is a portion of the display device.

4. The X-ray imaging apparatus of claim 3, wherein the projector controller is further configured to control a location of the active area of the display device, thereby controlling a location of the visible image projected by the projector.

5. The X-ray imaging apparatus of claim 2, wherein the projector controller is further configured to control a distance between each lens of the plurality of lenses, thereby controlling a size of the visible image projected by the projector.

6. The X-ray imaging apparatus of claim 2, wherein the projector controller is further configured to control a distance between each lens of the plurality of lenses, thereby controlling a focus of the visible image projected by the projector.

7. The X-ray imaging apparatus of claim 3, wherein the display device is a deformable mirror device (DMD).

8. The X-ray imaging apparatus of claim 3, wherein the display device is a liquid crystal on silicon (LCoS).

9. The X-ray imaging apparatus of claim 3, wherein the display device is an organic light emitting diode (OLED).

10. The X-ray imaging apparatus of claim 1, wherein the visible image comprises information regarding a imaging operation of the X-ray imaging apparatus or information regarding a target object to be photographed by the X-ray imaging apparatus.

11. The X-ray imaging apparatus of claim 1, wherein the main controller is configured to adjust an orientation of the optical apparatus.

12. The X-ray imaging apparatus of claim 1, wherein the optical apparatus is a revolving mirror.

13. The X-ray imaging apparatus of claim 1, wherein the optical apparatus is a beam splitter.

* * * * *